(12) United States Patent
Hart et al.

(10) Patent No.: US 10,595,890 B2
(45) Date of Patent: *Mar. 24, 2020

(54) MINIMALLY INVASIVE LAPAROSCOPIC TISSUE REMOVAL DEVICE

(71) Applicants: Stuart Richard Hart, Tampa, FL (US); Erik James Esinhart, Tampa, FL (US); Adam Thomas Lytle, Cape Coral, FL (US); Daniel Ryan Kamsler, Land O' Lakes, FL (US); Charles William Drake, III, Tampa, FL (US); Yasin Ahamed Junaideen, St. Petersburg, FL (US); Mario Alves Simoes, Pinellas Park, FL (US)

(72) Inventors: Stuart Richard Hart, Tampa, FL (US); Erik James Esinhart, Tampa, FL (US); Adam Thomas Lytle, Cape Coral, FL (US); Daniel Ryan Kamsler, Land O' Lakes, FL (US); Charles William Drake, III, Tampa, FL (US); Yasin Ahamed Junaideen, St. Petersburg, FL (US); Mario Alves Simoes, Pinellas Park, FL (US)

(73) Assignee: University of South Florida, Tampa, FL (US)

( * ) Notice: Subject to any disclaimer, the term of this patent is extended or adjusted under 35 U.S.C. 154(b) by 264 days.

This patent is subject to a terminal disclaimer.

(21) Appl. No.: 15/828,225

(22) Filed: Nov. 30, 2017

(65) Prior Publication Data

US 2018/0085139 A1 Mar. 29, 2018

Related U.S. Application Data

(63) Continuation of application No. 14/817,434, filed on Aug. 4, 2015, now Pat. No. 9,861,380, which is a
(Continued)

(51) Int. Cl.
*A61B 1/00* (2006.01)
*A61B 17/32* (2006.01)
*A61B 17/00* (2006.01)

(52) U.S. Cl.
CPC .......... *A61B 17/32002* (2013.01); *A61B 2017/00685* (2013.01); *A61B 2017/320024* (2013.01)

(58) Field of Classification Search
CPC .... A61B 17/32002; A61B 2017/00685; A61B 2017/320024
See application file for complete search history.

(56) References Cited

U.S. PATENT DOCUMENTS 5,215,521 A 6/1993 Cochran et al.
5,443,472 A 8/1995 Li
(Continued)

FOREIGN PATENT DOCUMENTS

WO 2008010150 A2 1/2008
WO 2013016698 A1 1/2013

OTHER PUBLICATIONS

Canadian office action for Serial No. 2,900,017, dated Apr. 11, 2019, pp. 1-4.
(Continued)

*Primary Examiner* — Richard G Louis
(74) *Attorney, Agent, or Firm* — Nicholas Pfeifer; Smith & Hopen, P.A.

(57) ABSTRACT

A minimally invasive laparoscopic tissue removal device, namely a morcellator. The device includes, from proximal end to distal end, a handle, handle guard, elongate sheath, and mouth, finally terminating in a safety tip. The elongate sheath and mouth are concentric, such that two elongate, rotating cutting/shredding blades/teeth and one elongate auger feed screw can be positioned along the length of the
(Continued)

sheath and mouth. The teeth are opposingly disposed and staggered, such that contact with tissue mass grabs and pulls tissue inwards toward the auger, which transports the tissue proximally toward the outside of the patient's body. A motor unit and gear assembly can be coupled to the teeth and auger to drive rotation of the teeth and auger. A cup assembly can be disposed in overlying relation to the mouth for guiding the tissue mass towards the mouth. Various mechanisms of safely covering the mouth are contemplated as well.

25 Claims, 28 Drawing Sheets

Related U.S. Application Data continuation of application No. PCT/US2013/050085, filed on Jul. 11, 2013.

(60) Provisional application No. 61/821,941, filed on May 10, 2013, provisional application No. 61/760,892, filed on Feb. 5, 2013.

(56) References Cited

U.S. PATENT DOCUMENTS

| | | | |
|---|---|---|---|
| 5,520,634 A | 5/1996 | Fox et al. | |
| 5,562,694 A | 10/1996 | Sauer et al. | |
| 5,569,284 A | 10/1996 | Young et al. | |
| 5,591,187 A | 1/1997 | Dekel | |
| 6,039,748 A | 3/2000 | Savage et al. | |
| 6,468,228 B1 | 10/2002 | Topel et al. | |
| 7,226,459 B2 | 6/2007 | Cesarini et al. | |
| 7,510,563 B2 | 3/2009 | Cesarini et al. | |
| 8,282,572 B2 | 10/2012 | Bilsbury | |
| 9,861,380 B2 * | 1/2018 | Hart | A61B 17/32002 |
| 2002/0058956 A1 | 5/2002 | Honeycutt et al. | |
| 2007/0219549 A1 | 9/2007 | Marshall et al. | |
| 2008/0249553 A1 | 10/2008 | Gruber et al. | |
| 2008/0255597 A1 | 10/2008 | Pravong et al. | |
| 2010/0030216 A1 | 2/2010 | Arcenio | |
| 2011/0176403 A1 | 8/2011 | Robertson et al. | |
| 2011/0196400 A1 | 8/2011 | Robertson et al. | |
| 2013/0103067 A1 | 4/2013 | Fabro et al. | |

OTHER PUBLICATIONS

Peters. Minimally Invasive Surgery Expanded Version. American society of colon & rectal surgeons. Date Accessed Sep. 16, 2015. https://www.fascrs.org/patients/disease-condition/minimally-invasive-surgery-expanded-version.

Rutala et al., Guideline for Disinfection and Sterilization in healthcare facilities. 2008. CDC. Date Accessed Sep. 16, 2015: 1-158. http://www.cdc.gov/hicpac/Disinfection_Sterilization/13_0Sterilization.html.

DMU 60 P duoBLOCK. DMG MORI. Date Acessed: Sep. 16, 2015. http://en.dmgmori.com/products/milling-machines/universal-milling-machines-for-5-sided-5-axis-machining/dmu-p-duoblock/dmu-60-p-duoblock.

International Search Report for PCT/US2013/050085 (filing date: Jul. 11, 2013) dated Oct. 21, 2013; Applicant: University of South Florida et al.

International Preliminary Report of Patentability for PCT/US2013/050085 (filing date: Jul. 11, 2013) with a priority date of Feb. 5, 2013; Applicant: University of South Florida et al.

* cited by examiner

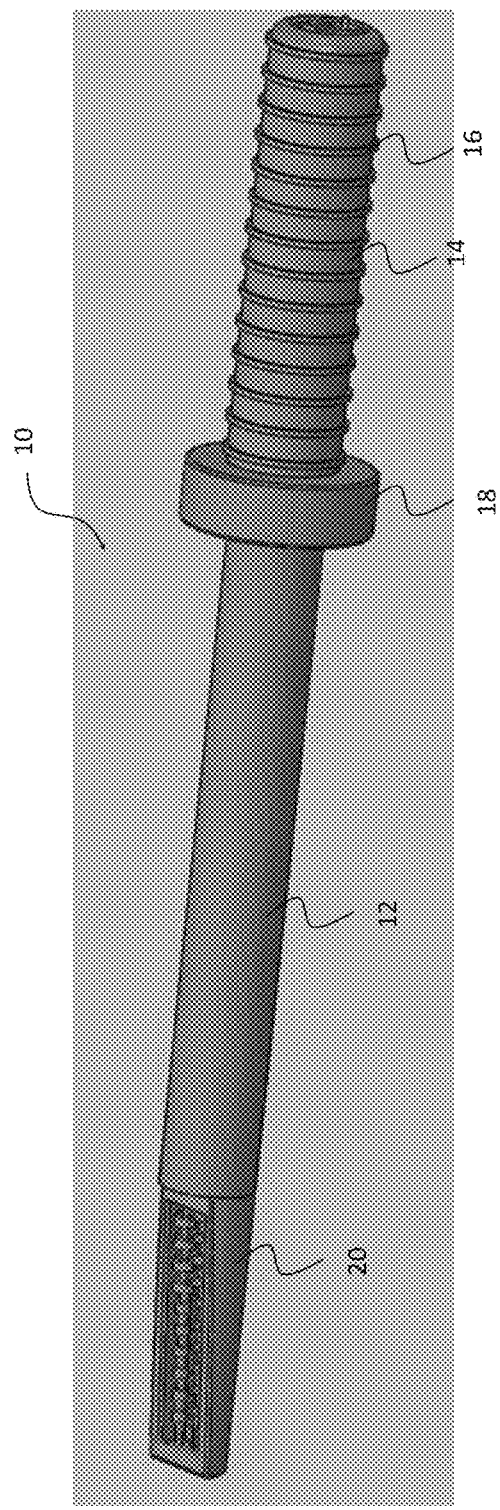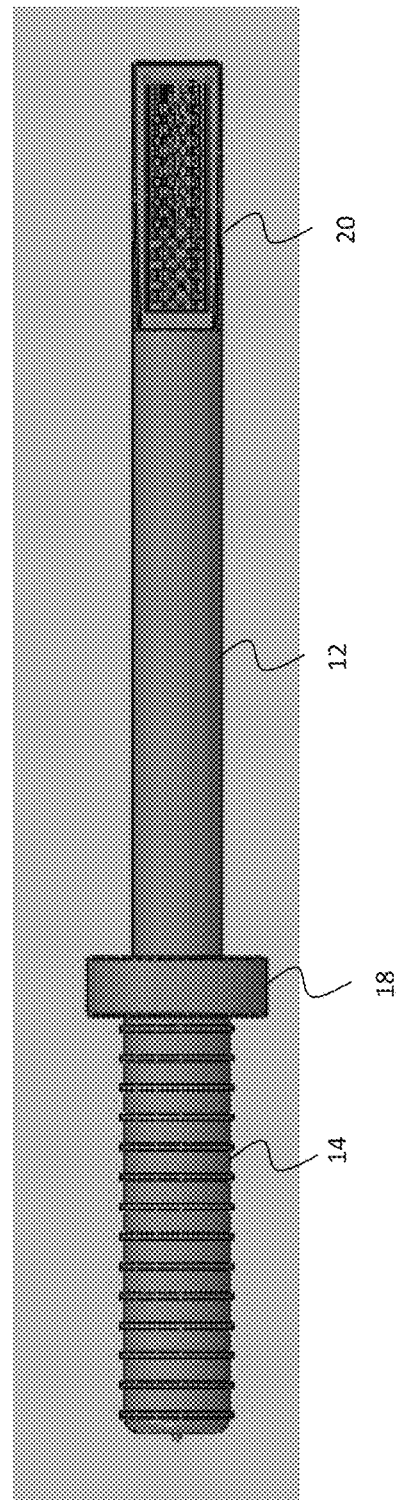
Fig. 1
Fig. 2

MINIMALLY INVASIVE LAPAROSCOPIC TISSUE REMOVAL DEVICE

CROSS-REFERENCE TO RELATED APPLICATIONS

This nonprovisional application is a continuation and claims priority to currently pending U.S. Nonprovisional patent application Ser. No. 14/817,434, entitled "Minimally Invasive Laparoscopic Tissue Removal Device", filed Aug. 4, 2015, which is a continuation of and claims priority to currently pending PCT Patent Application No. PCT/US2013/050085, entitled "Minimally Invasive Laparoscopic Tissue Removal Device", filed Jul. 11, 2013, which claims priority to U.S. Provisional Patent Application No. 61/760,892, entitled "Minimally Invasive Laparoscopic Tissue Removal Device," filed Feb. 5, 2013, and to U.S. Provisional Patent Application No. 61/821,941, entitled "Minimally Invasive Laparoscopic Tissue Removal Device," filed May 10, 2013, all of which are incorporated herein in their entireties.

BACKGROUND OF THE INVENTION

1. Field of the Invention

This invention relates, generally, to laparoscopic operations. More particularly, it relates to a morcellator for laparoscopic hysterectomies

2. Brief Description of the Prior Art

Laparoscopic surgery, a type of minimally invasive surgery, has increased over the past 10 years due to a dramatic decrease in post-operative patient recovery time, minimized risk of infections, less pain, and reduced scarring. Compared to traditional open cut surgery, laparoscopic surgery uses several small incisions from five (5) millimeters to fifteen (15) millimeters. These incisions are known as ports that hold hollow tubular trochars that are designed for the passing of instruments and devices. Typically, these ports are inserted through the subject or patient's abdominal wall into the peritoneal cavity to provide the surgeon with access to necessary organs. This complex system allows surgeons to perform surgeries with smaller incisions than traditional operations (ASCRS, 2008).

According to the U.S. Department of Health & Human Services, a hysterectomy (surgical removal of the uterus) is the second-most performed surgery (after cesarean section) on women in the United States with more than 600,000 of these operations performed each year. Of these, 42% were performed laparoscopically. It is estimated that one in three women in the U.S. has undergone a hysterectomy by the age of 60.

During hysterectomy laparoscopic surgeries, surgeons need clear visibility and range of device control at all times to avoid damaging nearby vital organs and blood vessels while reducing scars and pain for the patient. Depending on the severity and depth of the hysterectomy surgery, the operation can last from an hour to a few hours. This prolonged period of time, combined with repetitive hand actions, may cause strain and fatigue (Gale Encyclopedia of Medicine, 2008). These problems lead to concerns in designing more ergonomic devices that may reduce the overall safety of the operation for physicians and patients.

Several devices that may be considered to be internal tissue removal devices exist for use in laparoscopic surgery. Oftentimes, surgeons use a device called a morcellator to extract large tissue masses through these incisions by cutting the tissue into smaller segments. The GYNECARE MORCELLEX tissue morcellator is one of the oldest single-patient-use devices. The device is inserted into the patient and allows tissue to be grasped with a standard grasping instrument extended through the device's central lumen. The tissue can be drawn up manually inside the device's central lumen into the inner stationary sheath as the exposed blade cuts the tissue. The greatest shortcoming of the GYNECARE MORCELLEX tissue morcellator is the uncertainty of the exposed blade that can cause damage to vital organs that surround the abdomen (Zullo, 2012).

Another possible prior art device, LINA XCISE disposable laparoscopic morcellator, consists of similar features, and therefore has the same flaws, as the GYNECARE MORCELLEX, but provides a cordless disposable morcellator, intended for tissue morcellation during laparoscopic gynecological procedures.

Another commercial device known as the MYOSURE Tissue Removal System is a device having a distal end with a side window that rotates and reciprocates so as to cut tissue. Simultaneously, the cut tissue is sucked out of the body through the body/sheath of the device. The device has a diameter of about 6.5 mm, so although a smaller incision site is necessary, the targeted tissue must be broken down into significantly smaller portions for suction out of the body. Additionally, this device runs across similar flaws as previously described, such as remnants remaining in the body (particularly here where tissue must be broken down so much).

U.S. Pat. No. 7,510,563 to Cassidy et al. and U.S. Pat. No. 7,226,459 to Cassidy et al. have a similar cutting window with a cutting blade exposed when the window is opened. The blade is rotated, thereby cutting tissue and bringing the cut tissue into the cutting window for aspiration. However, to be cut, the tissue within the cutting window must catch on a sharp hook disposed on the opposite side of the cutting window as the blade. Then the blade slices the tissue and rotates to advance the tissue out of the body through a suction mechanism. Thus, the sharp hook and blade are exposed to peripheral tissue, and the cutting window significantly limits the amount of tissue that can be cut in an efficient manner.

Another example is U.S. Pat. No. 6,039,748 to Savage et al. This device utilizes a circular rotating blade to cut tissue while a grasping device is inserted through the proximal end of a sheath to the distal end of the sheath to manually grasp and pull tissue while the cutting blade cuts tissue. Savage is provides a device designed to fit inside the lumen of the morcellator, allowing the grasper to be inserted and removed while maintaining positive pressure within the abdomen of the patient. As the tissue is pulled proximally back through the lumen of the morcellator, the cutting blade cuts the tissue. However, this device requires excessive manual effort from the surgical team, it would be easy for a portion of the tissue to become entirely cut off from the remaining tissue and be improperly left within the subject.

U.S. Pat. No. 5,562,694 to Sauer et al. teaches a device designed with cutting teeth that reciprocate back and forth in a sawing motion to cut masses. The top of this device has cooperative jaw members that open and close in a jaw-like manner in order to grasp tissue. When the tissue is grasped, the saw blade is activated and cuts through the tissue in an effectuating remote reciprocal movement, as the jaw closes to encapsulate the mass. The device is designed to operate with a manual grasper inserted through the proximal end that extends from the sheath when the jaw is open to grasp and pull tissue within the device for cutting. However, the device requires manual manipulation of the grasper to remove tissue from the body. Additionally, the methodology of cutting, using a sawing motion, is inefficient and exposes surrounding tissue to being improperly cut.

U.S. Pat. No. 5,443,472 to Li discloses a morcellation system primarily consisting of two main mechanisms. One mechanism acts as a capture device to capture a tissue mass while the other mechanism acts as a morcellator to cut and remove tissue from the body. The mass is captured in a net-like, tissue containment structure that can articulate at an angle while the cutting device is positioned inside. The cutting device has a blade opening, and the net-like structure is used to squeeze the mass into the opening created by the blade opening. From this point, the surgeon squeezes the handle to close the blade, which cuts the tissue, and the action of opening the blade causes the piece of tissue that was cut to move proximally through the device. Within the device, barbs exist that allow only one way proximal movement through the tube of the device. As each additional piece of tissue is cut by the device, the newest piece of tissue within the tube pushes the last piece of tissue up towards the proximal end. However, the entirety of the mechanism of this device is manual and in particular relies on the grip of the surgeon's hand to actuate the cutting blade. The device itself provides several points of inefficiency and an excess of energy consumption required from the surgical team.

U.S. Pat. No. 5,520,634 to Fox et al. relates to a morcellator that is structured with a rotatable cutting head (e.g., a blade) and a motor that communicates the rotation of the cutting head, along with suction through the cutting head to aspirate the masses that are cut. The cutting head is "relatively retractable" but extends out of the sheath, thereby exposing the blade to other non-targeted tissue within the body. Further, the device is designed to go through an abdominal port and thus is limited to the size of the port.

U.S. Pat. No. 5,569,284 to Young et al. teaches a morcellator that includes a tubular portion with an elongated auger rotatably positioned within its bore. An aperture near the distal end of the tubular portion permits access for body tissue to contact the auger. However, the device is limited to fifteen (15) mm and is inserted in an abdominal port to come in contact with the tissue. Additionally, the auger has a cover flap over the aperture, where the cover flap that opens to allow the auger to contact the tissue for cutting and transporting out of the body. The cover flap opens at an angle and thus the amount of tissue that can be efficiently cut is quite limited.

U.S. Pat. No. 5,215,521 to Cochran et al. discloses a device that is designed to contain a bag within a sheath until the bag is deployed within a body to enclose and hold a mass within the body. The bag holds the mass in place to allow the surgeon to use a morcellator to break down the mass until the bag containing the morcellized mass can be removed through the device sheath and port. This device is focused on holding the material and attempting to reduce the amount of tissue that escapes when being morcellated. However, it appears that the organ must physically be placed into the bag prior to morcellation. This creates a larger burden on the surgical team. Additionally, there are many moving parts and complexities that may result in a malfunction of the device, particularly when deploying the bag within a body.

U.S. Pat. No. 6,468,228 to Topel et al. relates to a morcellator that includes a helical coil inserted through the hollow sheath and extends from the distal cutting end of sheath to embed into a tissue mass and affix itself in the mass. The helical coil then is pulled back with the tissue mass, and the cutting end of the sheath cores or morcellates the tissue mass until completion. This device suffers many of the drawbacks previously explained through traditional morcellation techniques. In particular, the tissue must be manually removed, and remnant tissue may remain within the body improperly.

U.S. Pat. No. 8,282,572 to Bilsbury teaches a bag deployment device that uses a sheath to guide and insert the bag into the body. The device uses a flexible metal to push and expand the bag/funnel once outside of the sheath. The bag is intended to capture the tissue within the body and fit within the sheath for removal outside of the body. The drawbacks of this device are that the tissue masses must be small enough for removal from the body, as the device does not morcellate the tissue, rather simply attempting to transport whole tissue outside of the body.

U.S. Pat. No. 5,591,187 to Dekel discloses a device that includes a hollow cylindrical sheath with a rotatable auger disposed therein for rotational cutting. The distal end of the auger includes a cutting blade outside of the sheath. Additionally, the distal end of the auger has an opening that receives a corkscrew-like structure that extends furthest distally from the auger and is used to engage the tissue mass to be cut. Thus, the corkscrew-like structure engages the tissue mass and positions the tissue mass for cutting by the serrated blade. Then the tissue is drawn into the sheath by the auger, which is being manually rotated by the user. Major drawbacks of this device include peripheral or extraneous tissue being exposed to both the cutting blade and the corkscrew-like structure. This may be particularly true when there are smaller pieces of tissue that need to be removed, and the corkscrew-like structure is incapable of engaging it. Additionally, the tissue must be extracted manually, and as such, small pieces of tissue may be left in the body. The device provides an inefficient and dangerous manner of removing tissue from a body.

The devices currently used for laparoscopic surgeries lead to problems that are evident during an operation. These problems include lack of proper cutting efficiency, safety concerns, and excessive scarring. As indicated, a wide variety of different morcellation devices have been used in attempts to facilitate tissue removal, but there has been no growth for an effective cutting design.

Accordingly, what is needed is an improved streamlined morcellation cutting device for laparoscopic surgeries that is safe and effective during and after surgery. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an automated, efficient, accurate, and safe morcellator with all-in-one design is now met by a new, useful, and nonobvious invention.

In an embodiment, the current invention is a morcellator for removing a targeted tissue mass inside the body of a subject or patient through a laparoscopic port or vagina of the subject or patient. The morcellator includes a gripping apparatus for stabilizing the morcellator when it is inserted into the patient's body. An elongate sheath is included and has proximal and distal ends. The proximal end of the sheath is coupled to the gripping apparatus. The distal end of the sheath is coupled to a mouth, which has a substantially hollow interior. The mouth has a window that allows open communication between the interior of the mouth and the external environment. Internal to the morcellator, a pair of elongate jaws extends within the interior of both the sheath and the mouth. The jaws are positioned in fixed, spaced relation to each other. The distal portion of each jaw has blades to cut the tissue to be morcellated. The blades can take on a variety of configurations including blades positioned essentially in alignment with the jaw, perpendicular to the jaw, diagonally aligned down the length of the jaw, or any combination thereof. These blades can be aligned along each jaw, similar to teeth that oppose the teeth on the other jaw. The blades cut or shred the tissue and draw it inwardly toward the inside of the mouth via rotation of the jaws. The morcellator further includes an auger that extends within the interior of both the sheath and the mouth. The auger is positioned in fixed, spaced relation underneath the jaws. The auger transports the cut or shredded tissue proximally toward the gripping apparatus and out of the body via rotation of the auger. The morcellator further includes a control apparatus that control the rotation of the jaws and the auger.

The gripping apparatus may be a handle conformed to a user's hand. In a further embodiment, this handle may be a pistol grip positioned in perpendicular relation to the longitudinal axis of the sheath.

The sheath and mouth may be formed from a single piece.

There may be three (3) elongate channels along the interior of the sheath. The channels are structured to snugly fit the two jaws and auger, respectively.

The morcellator may further include a cup assembly positioned in overlying relation to the window of the mouth. The cup assembly would have an open top with top edge and open bottom with bottom edge. The bottom edge would be attached to the outer edges of the window. The top edge would be formed of a wire frame that stabilizes the cup assembly in an upright position. In a further embodiment, the interior of the sheath can include a supplementary channel, such that the cup assembly can be partially folded into the supplementary channel, while remaining attached to the outer edges of the window, thus covering the window in the compressed position. In yet a further embodiment, a deploy apparatus can be included that fits in the supplementary channel, such that it can deploy the cup assembly from its compressed position into an upright/expanded position.

The morcellator may further include a safety tip at the distal end of the morcellator. The safety tip can manipulate or push extraneous tissue to better reach or target the tissue mass.

The morcellator may further include a cover apparatus for covering or filling the window of the mouth. The cover apparatus typically would have a closed position that protects extraneous tissue from the teeth or blades and an open position that exposes the teeth to the tissue.

In a further embodiment, the cover apparatus can be a bay rotating outer sheath disposed in outer relation to the mouth. This outer sheath would have a cutout that is at least as big as the window. When this outer sheath is rotated, exposure of the window can be controlled. Maximum exposure would occur with the cutout is maximally aligned with the window. In another embodiment, the cover apparatus can be a bay sliding outer sheath disposed in outer relation to the elongate sheath and mouth. This outer sheath is slidable in a proximal-distal direction to cover and uncover the mouth.

The control apparatus may include a motor unit and gear assembly in communication with each jaw and the auger. In a further embodiment, the gear assembly can be a plurality of spur gears with a specific configuration as follows. A driving gear is securely coupled to the auger. A first driven gear is meshably engaged to the driving gear. A conjointly-rotating driving gear is positioned in fixed spaced relation to the first driven gear and is concentric with the first driven gear. The conjointly-rotating driving gear is securely coupled to one of the jaws. A second driven gear is meshably engaged to the conjointly-rotating driving gear. The second driven gear is securely coupled to the other jaw. Thus, rotation of the initial driving gear rotates the plurality of gears, the jaws, and the auger.

A set of teeth associated with one jaw and another set of teeth associated with the other jaw can have a staggered, interlocking relationship with each other.

The morcellator may further include hook-like protrusions disposed on the teeth to facilitate drawing the tissue mass inwardly between the jaws toward the auger.

Activation of the morcellator by the control apparatus can rotate the jaws and auger simultaneously.

The elongate sheath may have a diameter greater than about twenty (20) millimeters.

The targeted tissue mass may be a uterus, such that removal of the uterus would be a hysterectomy.

In a separate embodiment, the current invention is a morcellator for removing a uterus of a subject or patient through a vagina of the subject or patient. The morcellator includes an elongate sheath having three (3) channels therewithin along the length of the sheath. The sheath has a maximum diameter of about thirty (30) millimeters. A pistol grip is coupled to the proximal end of the sheath in perpendicular relation to the sheath. A mouth is coupled to the distal end of the sheath and has a substantially hollow interior. A window in the mouth provides open communication between the interior of the mouth and the external environment. Internal to the morcellator, a pair of elongate jaws is disposed within two (2) of the three (3) channels within the sheath. The jaws extend into the interior of the mouth. The jaws have opposing teeth that have a staggered, interlocking relation with each other and draw the uterus inwardly between the jaws. The morcellator further includes an auger in the third channel of the three (3) channels in the sheath. Each of the three (3) channels have spaced relation to each other. While the jaws lie on the same horizontal plane as each other, the auger lies beneath the jaws and is substantially centered between the jaws. The jaws cut or shred the uterus, whereas the auger transports the cut or shredded uterus proximally out of the patient's body. A safety tip is positioned at a distal end of the morcellator to push or manipulate extraneous tissue to reach or target the uterus. The morcellator further includes a cover apparatus for covering or filling the window of the mouth. The cover apparatus has a closed position for protecting extraneous tissue from the teeth and an open position for exposing the teeth to the tissue. A motor unit and gear assembly are also coupled to the jaws and auger for controlling the simultaneous rotation of the jaws and auger. The gear assembly is configured as follows. A driving gear is securely coupled to the auger. A first driven gear is meshably engaged to the driving gear. A conjointly-rotating driving gear is positioned in fixed spaced relation to the first driven gear and is concentric with the first driven gear. The conjointly-rotating driving gear is securely coupled to one of the jaws. A second driven gear is meshably engaged to the conjointly-rotating driving gear. The second driven gear is securely coupled to the other jaw. Thus, rotation of the initial driving gear rotates the plurality of gears, the jaws, and the auger.

In a separate embodiment, the current invention is a method of morcellating a targeted tissue mass inside the body of a female subject or patient. A morcellator is inserted into the vagina of the patient to reach the targeted tissue mass. The morcellator comprises a gripping apparatus for stabilizing the morcellator when inserted into the patient, an elongate sheath coupled to the gripping apparatus on its proximal end, and a mouth coupled to the distal end of the sheath. The morcellator further comprises a pair of elongate jaws extending along the interiors of the sheath and mouth, where the jaws have opposing teeth. The morcellator also includes an auger extending along the interiors of the sheath and mouth underneath the jaws. The morcellator further includes a control apparatus for controlling rotation of the jaws and auger. Once inserted into the body, the morcellator is actuated or activated to initiate rotation of the jaws and auger. The teeth of the morcellator contact the targeted tissue mass and draws the tissue inwardly toward the auger. The auger transports the tissue proximally toward the gripping apparatus and out of the patient's body.

The targeted tissue may be a uterus, whereby removal of the uterus is a hysterectomy.

The elongate sheath may have a diameter greater than about twenty (20) millimeters, since the morcellator is to be inserted into a vagina and not a conventional laparoscopic port in the abdomen.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 1 is a perspective view of an embodiment of the invention.

FIG. 2 is a top view of the embodiment of FIG. 1.

FIG. 23b is an upper perspective wireframe view of the embodiment of FIG. 23a.

FIG. 23c is a rear perspective wireframe view of the embodiment of FIG. 23a.

FIG. 23d is a side wireframe view of the embodiment of FIG. 23a.

FIG. 25b is a wireframe view of FIG. 25a.

FIG. 25c is a rear perspective wireframe view of the mouth depicted in FIG. 25a.

FIG. 26 is an exploded view of the mouth of FIG. 25a.

FIG. 28b is front perspective, close-up wireframe view of the gear assembly of FIG. 28a.

FIG. 29b is a front perspective view of the cup assembly of FIG. 29a.

DETAILED DESCRIPTION OF THE PREFERRED EMBODIMENT

Figure 3:
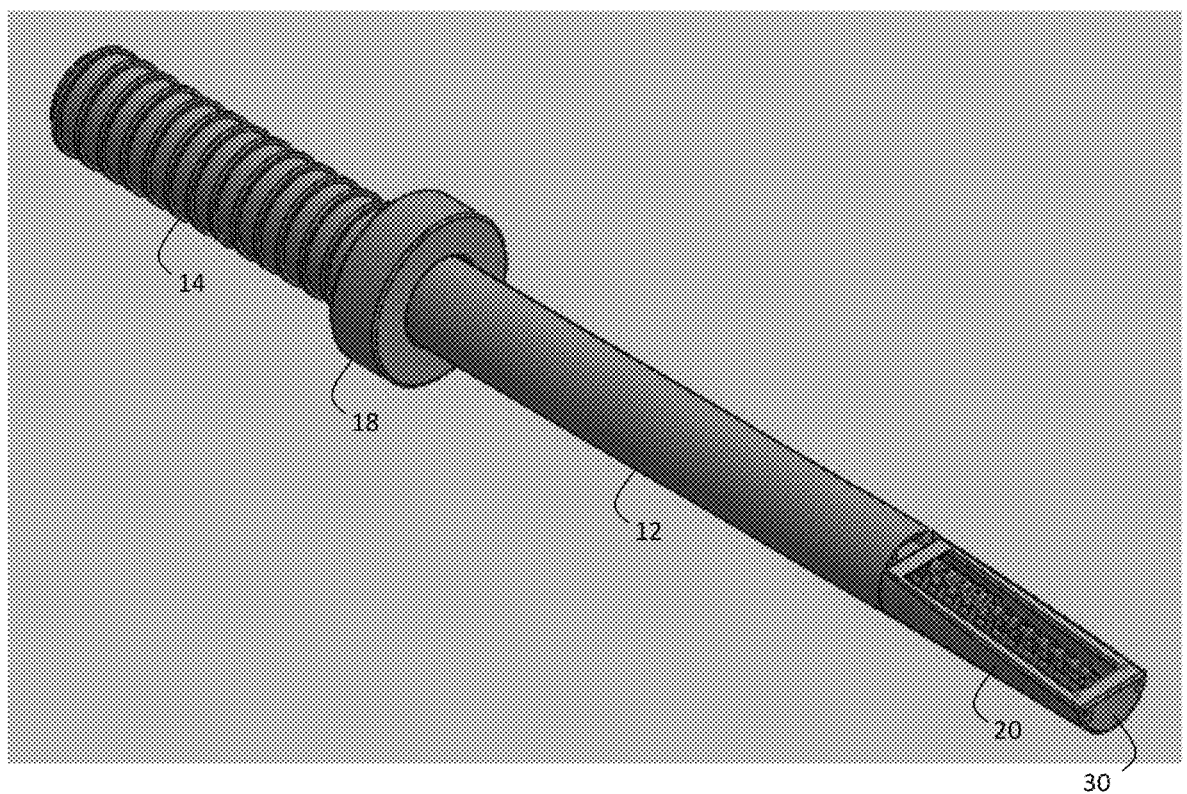
FIG. 3 is a perspective view of the embodiment of FIG. 1.
Figure 4:
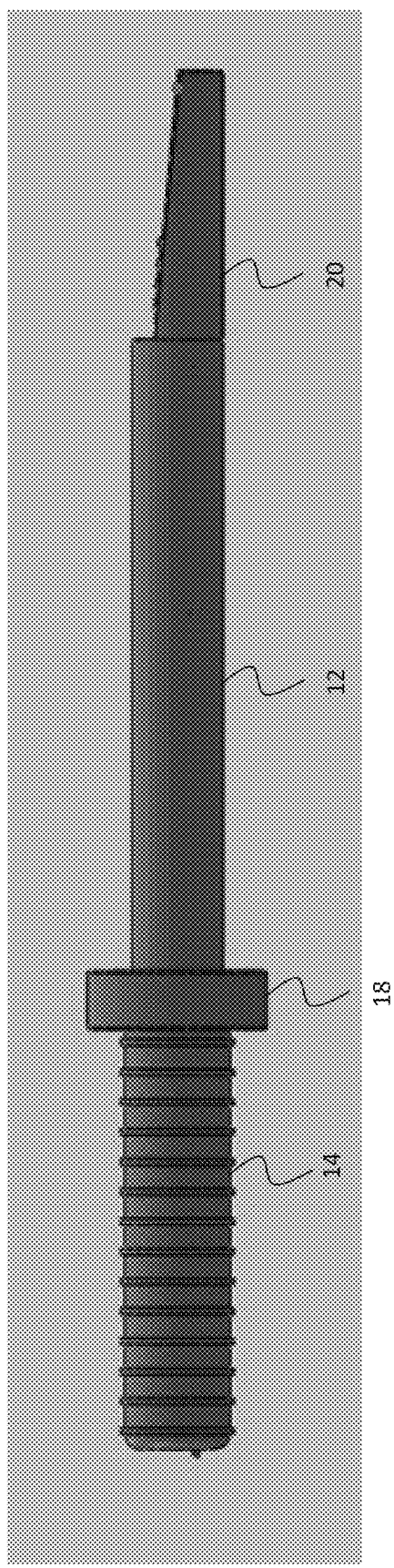
FIG. 4 is a side view of the embodiment of FIG. 1.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

During hysterectomy laparoscopic surgeries and laparoscopic surgeries generally, surgeons need to have clear visibility and device control at all times to avoid damaging nearby vital organs and blood vessels while reducing scars and pain for the patient all in a timely and efficient manner. The objective of this medical device design was to design a safe, ergonomic, and time efficient appropriate laparoscopic tissue removal device for use during traditional and complex hysterectomy surgeries, among other procedures in the pelvic region. Surgeons also face the problem of tissue being left behind within the body cavity during surgery; this invention aims to reduce the possibility of this problem. The primary advantage of the design reported is its ability to cut and transport tissue in an all in one design. This advantage allows the device to have a retractable sheath that safely houses the cutting blades. The sheath can then be used as an adjustable blade barrier to allow an increase or decrease in surface area of the blade exposed. This design will reduce surgery time, while reducing surgical fatigue.

The device is utilized for cutting, coring, and extracting tissue during laparoscopy operations. In an embodiment, the device consists of a handle, hand guard, hollow retractable sheath, barrel, auger for tissue transportation, cup assembly, and two spiral-cutting rotating blades housed at the end of the barrel. The interaction of the device with the tissue is a direct touch interaction. The sheath of the morcellator is inserted in the vaginal port. Once the distal end of the sheath is inserted, the cutting blades are engaged in a rotational motion, and tissue contact may begin on the opening side of the sheath. Once cut, the cutting auger transports the tissue down the sheath to the proximal end where it can be removed.

The device has two blades that are counter rotating at the face of the device. In an embodiment, these blades interlock with each other or are otherwise staggered and can have small hook like protrusions, which are designed to grasp and pull tissue inwards. While the tissue is being pulled in by these hooks, the sides of the blades are designed to cut and pull the tissue in the device towards the auger. The inside of the morcellator has an auger feed screw which rotates to motivate the cut tissue transport down the barrel and out of the body. While the blades and auger are in motion, the surgeon can adjust how much tissue needs to be cut by moving the retractable sheath to allow for an increase or decrease in surface area on the exposed blades. In order to help guide the tissue to the morcellator during a procedure, the end of the device can expose a cup shaped material. This material would allow the tissue to be placed in the cup and to be guided to the cutting blades while keeping smaller tissue pieces in one area.

The present invention aims to make laparoscopic surgeries safer, more efficient, and less stressful for the physician and surgical team by providing a device and methodology that can remove tissue faster while protecting or housing the blade for safety of the subject or patient's internal bodies and extraneous tissues. In an embodiment, the device is a surgical morcellation device that can be used during hysterectomies to remove various degrees of uterine tissue through a vaginal port.

The invention comprises a device that provides a safe solution to the problems referenced in the prior art by increasing the size of the barrel shaft and using a larger port that is inserted into the vagina to reduce surgery time. The vagina serves as a natural portal into the abdominal cavity, is easily distensible to accommodate larger incisions for wider diameter instruments, and leaves no visible abdominal scar.

In an embodiment, the structure of the current invention includes spiral feed blades and an auger, both of which are used to transport the tissue down the device. The structure further includes a retractable sheath that safely houses the blades, thereby providing an adjustable blade surface area. The current invention makes morcellation surgeries safer and more effective for women by reducing scarring and recovery time and not requiring additional incisions to be made into their abdominal cavities.

One objective of the invention is to provide a safe, ergonomic, and time-efficient laparoscopic tissue removal device for use during traditional and complex hysterectomy surgeries. Surgeons are often confronted with the problem of tissue being left behind within the body cavity during surgery; the current invention aims to reduce the possibility of this problem.

The invention is a significant advancement over the prior art because it has both a larger barrel and an auger feed screw for increased flow along with a cup assembly and tip for superior safety in certain embodiments. One of the advantages of an embodiment of the present invention is a closed safety tip at the end of the device that significantly reduces the risk of an exposed blade during a procedure. The improved design enhances the user experience for physicians, hospitals, and medical institutions.

A significant advantage of the apparatus is its ability to both cut tissue and transport tissue in a single apparatus. The device can include a variety of cover mechanisms that safely houses the cutting blades, for example a retractable sheath. A retractable sheath can be used as an adjustable blade barrier to allow an increase or decrease in surface area of the blade exposed. This design, among others with certain cover mechanisms reduce surgery time, while reducing surgical fatigue of the surgical team.

The device can be used for cutting, coring, and extracting tissue during laparoscopy operations. The device includes a handle, a hand guard, a hollow retractable sheath, a barrel, an auger for tissue transportation, a cup assembly, and two spiral-cutting rotating blades housed at the end of the barrel. The interaction of the device with the tissue is a direct touch interaction.

Methodologically, the sheath of the morcellator is inserted into the vaginal port. Once the distal end of the sheath is inserted, the cutting blades are engaged in a rotational motion, and tissue contact may begin on the opening side of the sheath. Once cut, the cutting auger transports the tissue down the sheath to the proximal end where it can be removed. The terms "proximal" and "distal" refer to spatial positions relative to the subject or patient; thus, the proximal end of the sheath is the end of the sheath closer to the subject or patient than the distal end of the sheath. In other words, the distal end of the device is the cutting end inside of the body, and the proximal end of the device is the gripping end outside of the body.

In an embodiment, the present invention is a minimally invasive laparoscope surgical morcellation device used during hysterectomies to remove various degrees of uterine tissue. Compared to the traditional procedures using a morcellator from a top-down approach into the abdomen by moving the device to the tissue, the present invention reverses the process to a bottom-up approach through a new vaginal port/platform. This embodiment of the present invention implements this new platform, which is structured specifically for entry through the vagina. The vagina serves as a natural portal into the abdominal cavity, is easily distensible to accommodate larger incisions for wider diameter instruments, and leaves no visible abdominal scars. Thus, having the port relocated to the vagina dramatically decreases the risk of herniation, provides surgeons with a platform for a wide variety of tools and devices, and decreases strain on the physician's hands.

Some of the main advantages of the device are its ability to cut and transport tissue in an all-in-one design and a barrel diameter that is double the size of a regular morcellator. The present invention is used for cutting, shredding, and extracting tissue. The interaction of the device with the tissue is a direct touch interaction. The sheath of the present invention is inserted in the vaginal port and mounted in place. Once the distal end of the sheath is inserted, a cup assembly can be pushed out manually to uncover the cutting blades and provide a funnel like flow for the tissue to be excised by the cutting blades. The cutting blades are then engaged in a rotational motion and tissue contact is initiated by surgical team bringing the tissue to the device using abdominal ports. Once the tissue is cut, the auger transports the tissue particles down the sheath to the proximal end where it can be removed.

The device has two (2) blades that are counter-rotating at the face of the device. These blades interlock with each other or are otherwise staggered and have small hook-like protrusions, which are designed to grab and pull tissue inwards. While the tissue is being pulled in by these hooks the sides of the blades are designed to cut and pull the tissue in the device towards the auger. The inside of the morcellator has an auger feed screw that rotates to help transport the cut tissue down the barrel and out of the patient's body. While the blades and auger are in motion, the surgeon can adjust how much tissue that needs to be cut by moving the retractable sheath, thereby permitting an increase or decrease in the surface area on the exposed blades. In order to help guide the tissue to the morcellator during a procedure, the distal end of the device can expose a cup-shaped material. This allows the tissue to be placed in the cup and guided to the cutting blades, while keeping smaller tissue pieces in one area.

In an embodiment, the present invention includes a handle, hand guard, barrel, auger for tissue transportation, cup assembly, closed safety tip, and two spiral-cutting rotating blades housed at the end of the barrel. The device is preferably made from medical grade stainless steel and thermoplastic for the handle and hand guard.

Increased Barrel Size

The present invention can have a barrel diameter of about thirty (30) mm, which is double size of a traditional morcellator with a standard diameter of only fifteen (15) mm. The present invention size increase is due to the vaginal platform having a 35 mm opening to accommodate larger devices. Having a larger barrel size provides a greater removal rate for the unwanted tissue, thus causing a decrease in surgery time. The increased outer diameter allows for an increase if the interior barrel diameter to 28 mm, which allows for an increase in the auger size, thus more efficient removal of the excised tissue.

Auger Transporter

The interior of the sheath/barrel of the present invention has an auger feed screw that rotates to help transport cut tissue down the barrel and out of the body for proper disposal. The auger increases the tissue removal rate, thus decreasing the total time of an operation.

Cup Assembly

In order to help guide the tissue to the distal end of the morcellator during a procedure, the end of the device can expose a cup shaped material or assembly. This allows the tissue to be placed in or scooped by the cup and guided to the cutting blades. The cup also serves as a safety barrier to keep all tissue masses (small, medium, large) in one area so that no tissue pieces are left behind in the body.

It is envisioned that the morcellator can be manufactured with the cup assembly built into the morcellator. Alternatively, the cup assembly can be a separate attachment. The cup assembly will become more apparent as this specification continues.

Safety Tip

The morcellator of the current invention may include a closed tip added to the distal end of the morcellator. This feature eliminates the need for the tip of the morcellator to approach the organ being removed directly. The tip can be rested, if needed, on parts of the body that are not intended to be punctured, cut, or removed during the surgery. This reduces the chance of an incident occurring due to physician fatigue or misjudgment.

Blades

In an embodiment, the device can have two spiral blades that counter-rotate at the face of the device. The blades interlock with each other and can have small hook-like protrusions, which are designed to grab and pull tissue inwards. As the blade hooks pull in the tissue, the sides of the blades are designed to cut and pull the tissue in the barrel towards the auger.

Sterilization

Sterilization is a major component when dealing with any medical device or instrument that will be in contact with the human body. The Centers for Disease Control and Prevention ("CDC") lists a number of sterilization requirements for different types of surgical devices. Any device that has contact with bodily fluids or tissues during routine use is considered to be a critical item that needs to be 100% sterile to reduce the chances of microbial transmission (Rutala & Weber, 2009). The present invention falls under this category and as such will require complete sterilization prior to packaging. Based on the acceptable sterilization practices listed by the CDC the most reliable way to sterilize the present invention will be a 20 minute dip into peracetic acid, which is a chemical that can be used at 50° C. to sterilize medical parts made of metal and or plastic without compromising the integrity of the material.

Example 1

Figure 14:
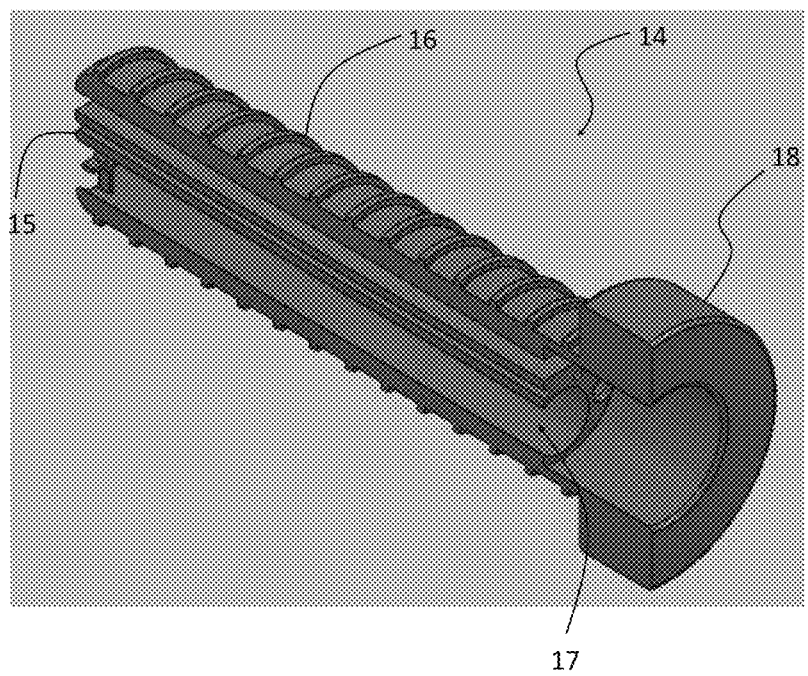
FIG. 14 is a perspective cross-sectional view of the handle of FIG. 13.
Figure 15:
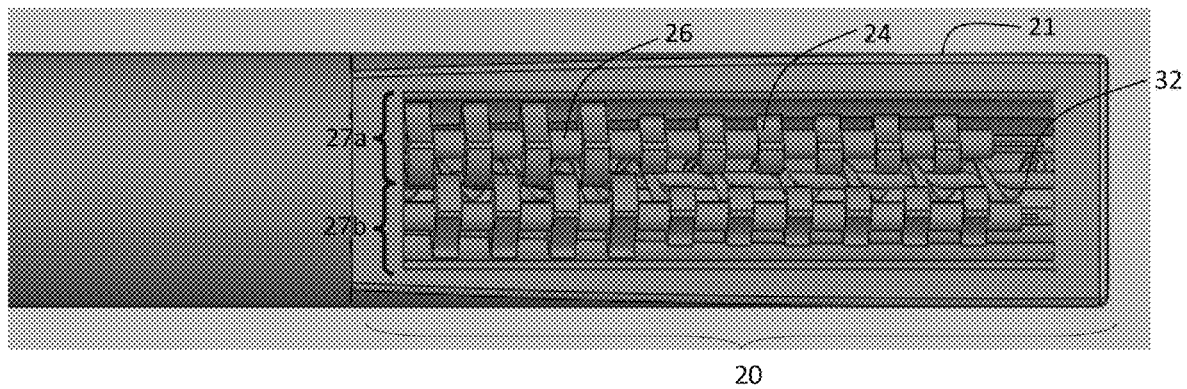
FIG. 15 is a top view of the mouth of an embodiment of the current invention, in particular depicting the teeth, drive shafts, and auger contained therein.

In an example, depicted in various aspects in FIGS. 1-15, the current invention is a laparoscopic morcellator denoted generally by the reference numeral 10. Morcellator 10 includes three distinct aspects: handle 14, sheath 12 containing hollow lumen 13 (FIG. 12), and mouth 20 containing drive shafts 26 with interlocking teeth 24 attached thereto and disposed therearound (FIG. 15).

Handle 14 is typically cylindrical and adapted to conform to a user's hand, though any structure or conformation is contemplated. Grooves 16 may be disposed on handle 14 to provide an ergonomic design. Other types of ridges, grooves, finger indentations, and the like are contemplated by the current invention to enhance the comfort of the user and/or function of the overall structure.

Figure 13:
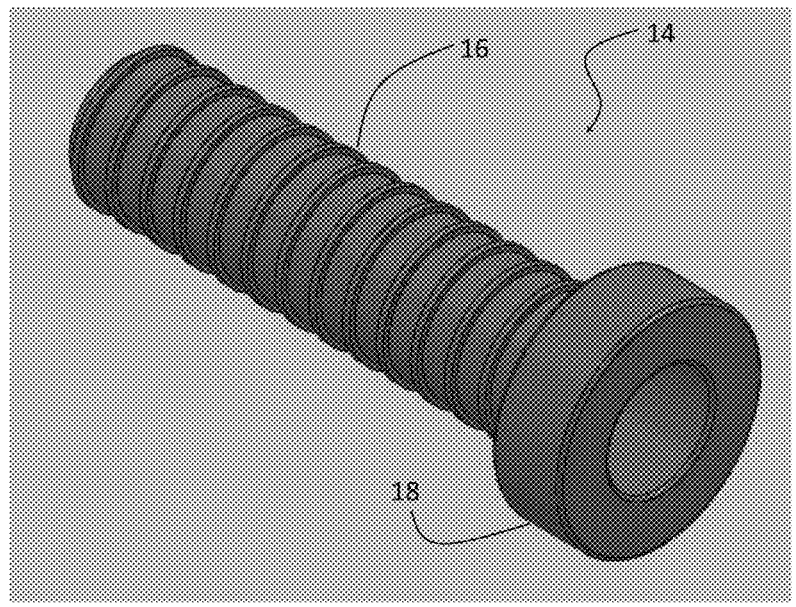
FIG. 13 is a perspective view of a handle as used in an embodiment of the current invention.

Handle 14 may be connected to mouth 20 through auger 32 or other cylinder (e.g., cylinder 15) disposed within the hollow lumen of sheath 12. In an embodiment, handle 14 can be hollow, as indicated in FIGS. 13 and 14, to facilitate this connection to mouth 20. Thus, handle 14 may be rotatable about sheath 12 and can be detachable from sheath 12 to allow for other types of handles to be connected. If handle 14 is connected to mouth 20, then rotation of handle 14 would rotate mouth 20 to allow mouth 20 to have flexibility to contact various surrounding tissues within the body. Alternatively, handle 14 may include blade operating handle or tool (not shown), the rotation of which can rotate mouth 20 or teeth 24 of mouth 20.

Handle guard 18 can be positioned between sheath 12 and handle 14 to protect the user's hand and to prevent morcellator 10 from being fully inserted into the body of the subject.

Figure 12:
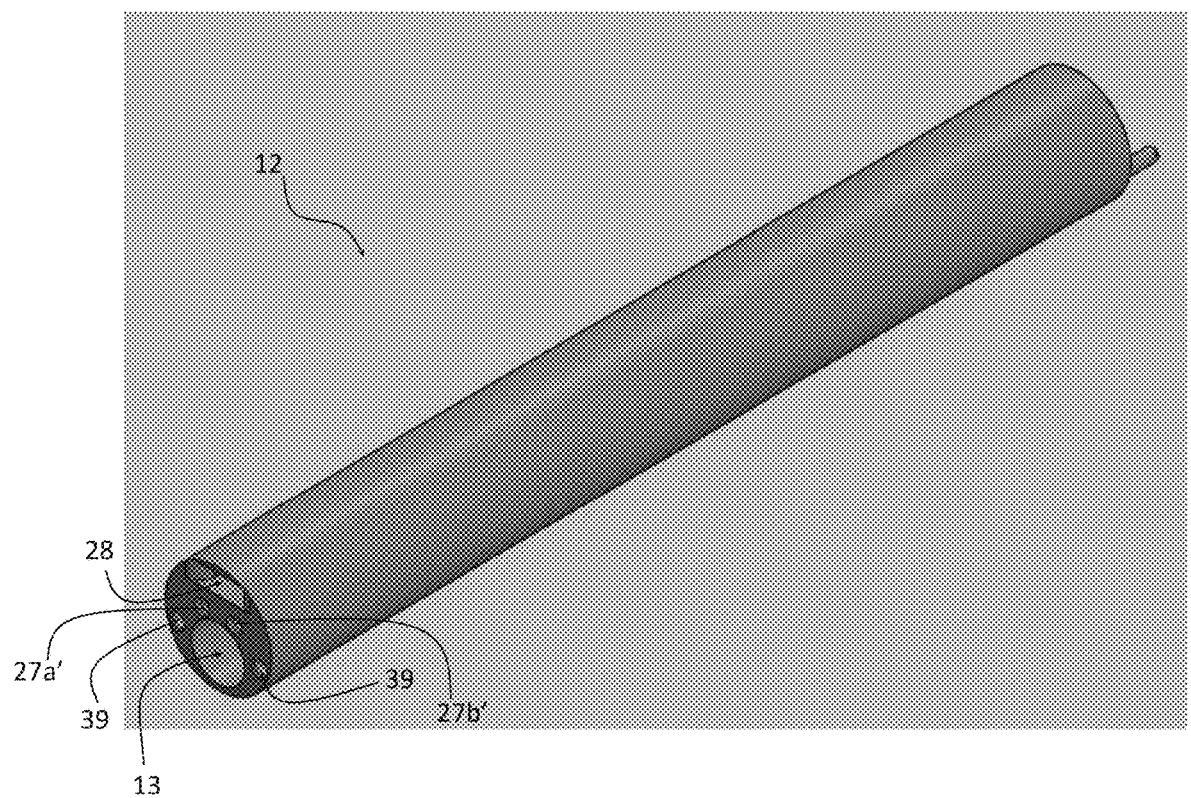
FIG. 12 is a perspective view of the sheath of the embodiment of FIG. 1.

Sheath 12 is elongate and includes hollow lumen 13, as indicated in FIG. 12, disposed along the longitudinal extent of the interior of sheath 12. Sheath 12 further includes a proximal end and a distal end, where the proximal end is attached to handle 14 extending therefrom and the distal end is in communication with mouth 20 extending therefrom. The distal end of sheath 12 telescopically receives mouth 20, such that mouth 20 can retract within hollow lumen 13 of sheath 12 and can rotate inside and outside hollow lumen 13 of sheath 12.

Sheath 12 further includes supplementary channel 28 that has an exit point on the proximal end of sheath 12 and an exit point on the distal end of sheath 12. Supplementary channel 28 has a hollow interior running along the length of sheath 12. Channel doors 29 may be included on the proximal end of sheath 12 and/or on the distal end of sheath 12. Channel doors 29 are used to close off either or both exit points of supplementary channel 28, so the interior of the body of the subject is not in open communication with the external environment through channel 28. For example, this is done so that extraneous materials cannot erroneously fall into the body of the subject from the external environment through channel 28. When open, supplementary channel 28 can be used for a variety of reasons. For example, a laparoscopic camera can be inserted through channel 28, so that the surgical team can view the procedure without the need to create an additional laparoscopic port in the subject's body.

Figure 17:
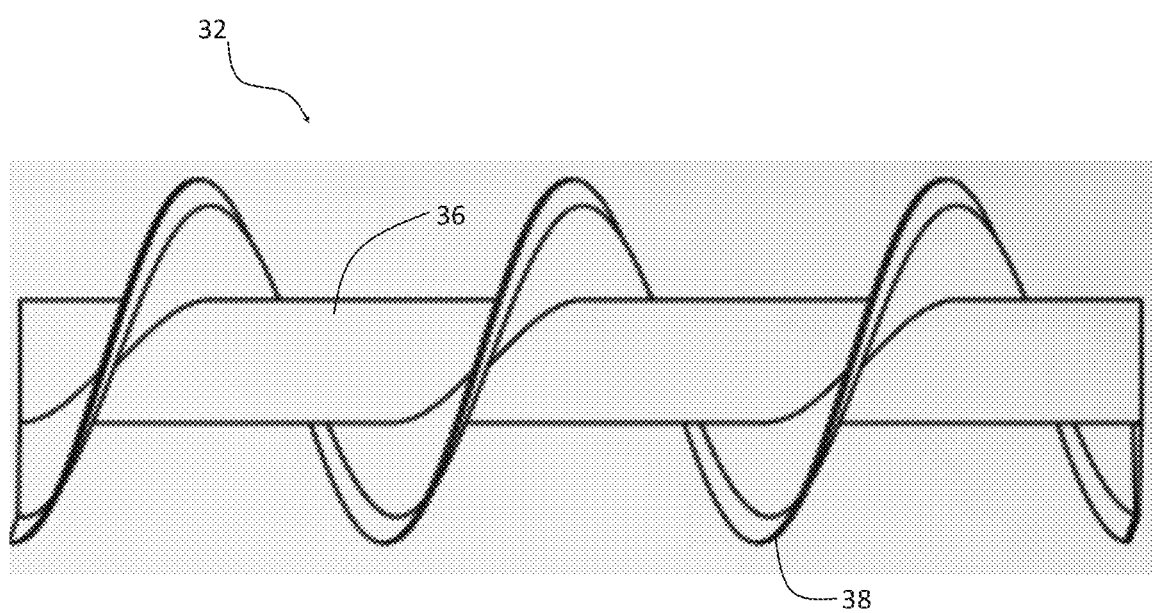
FIG. 17 is a side view of an auger transporter utilized in an embodiment of the current invention.

As depicted in FIG. 17, auger 32 includes elongate axle 36 and helicoid 38 disposed therearound along the length of elongate axle 36, thereby resembling the threads of a wood screw, though the current invention contemplates round or abnormally shaped (e.g., hexagonal) augers. Auger 32 is positioned within hollow lumen 13 of sheath 12 along the length of sheath 12. Auger 32 further extends into the substantially hollow interior of mouth 20 and is positioned in internal relation to teeth 24 and drive shafts 26 relative to mouth casing 21, such that auger 32 is enclosed within sheath 12 and is nearly enclosed within mouth 20 but is in communication with the external environment through the spaces among teeth 24. Optionally, auger 32 may further extend into the hollow interior of handle 14, dependent on the type of handle that is used with morcellator 10. Auger 32 is structured to rotate about the longitudinal axis within hollow lumen 13 and the interior of mouth 20. When tissue or other material comes into contact with auger 32 during rotation, the material can be further morcellated by helicoid 38, drawn up lumen 13 and transported along the longitudinal extent of sheath 12. The extent of morcellation and speed of transportation can be dependent on the rotational force of auger 32 and the preset pitch of the ribs of helicoid 38. A sharper pitch would encourage a larger distance of transportation of a tissue mass per turn of auger 32. A flatter pitch would encourage a smaller distance of transportation of the tissue mass per turn of auger 32.

The proximal end of auger 32 may be coupled to handle 14 such that manual or automated rotation of handle 14 would proportionately rotate auger 32. Alternatively, the proximal end of auger 32 may be electrically coupled to a drive shaft and motor (not shown) for automated activation, deactivation, and control of the rotation of auger 32. Auger 32 drives morcellated tissue toward the exterior of the body (e.g., toward handle 14) and out of the body of the subject. Auger 32 may also be rotated in the opposite direction, such that the tissue mass can be directed toward mouth 20.

Figure 10:
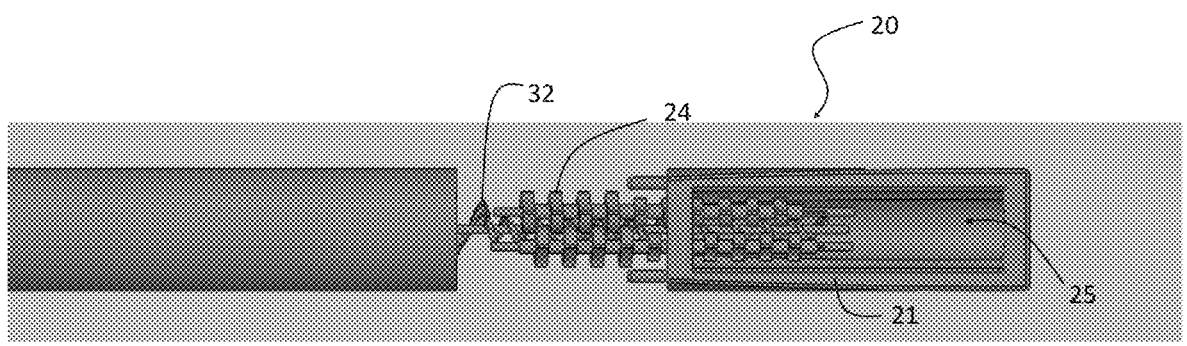
FIG. 10 is a top exploded view of the distal end, in particular the mouth, of the embodiment FIG. 1.
Figure 11:
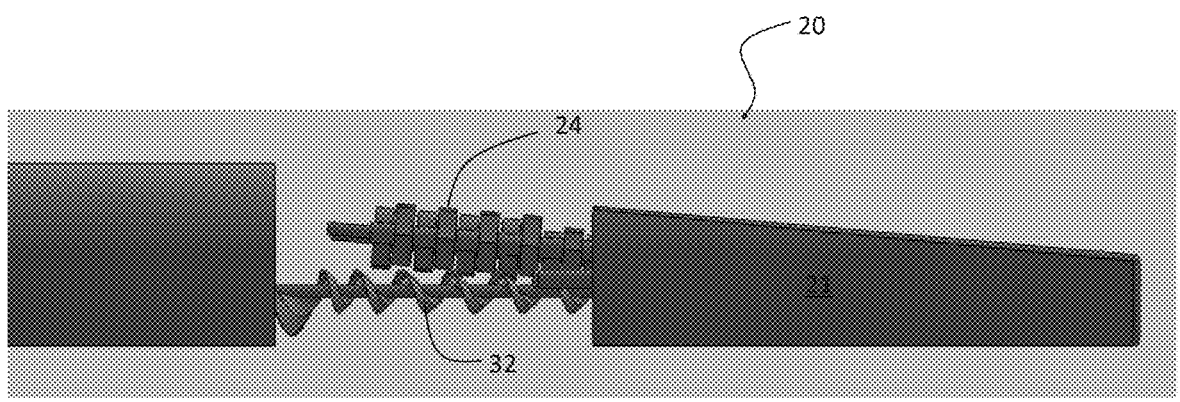
FIG. 11 is a side exploded view of the distal end, in particular the mouth, of the embodiment FIG. 1.

As depicted in FIGS. 10, 11, and 15, mouth 20 is disposed on and extends from the distal end of sheath 12. Mouth 20 includes mouth casing 21, teeth 24, drive shafts 26, and window 25, and contains the proximal end of auger 32. Mouth casing 21 is formed of a protective material and protects the substantially hollow interior of mouth 20 on all sides other than window 25 (FIG. 10). Window 25 leads from the external environment into the substantially hollow interior of mouth 20, such that the interior is in communication with the external environment via window 25. Auger 32 extends longitudinally from interior 13 of sheath 12 into the substantially hollow interior of mouth 20 at the distal end of morcellator 10.

Figure 6:
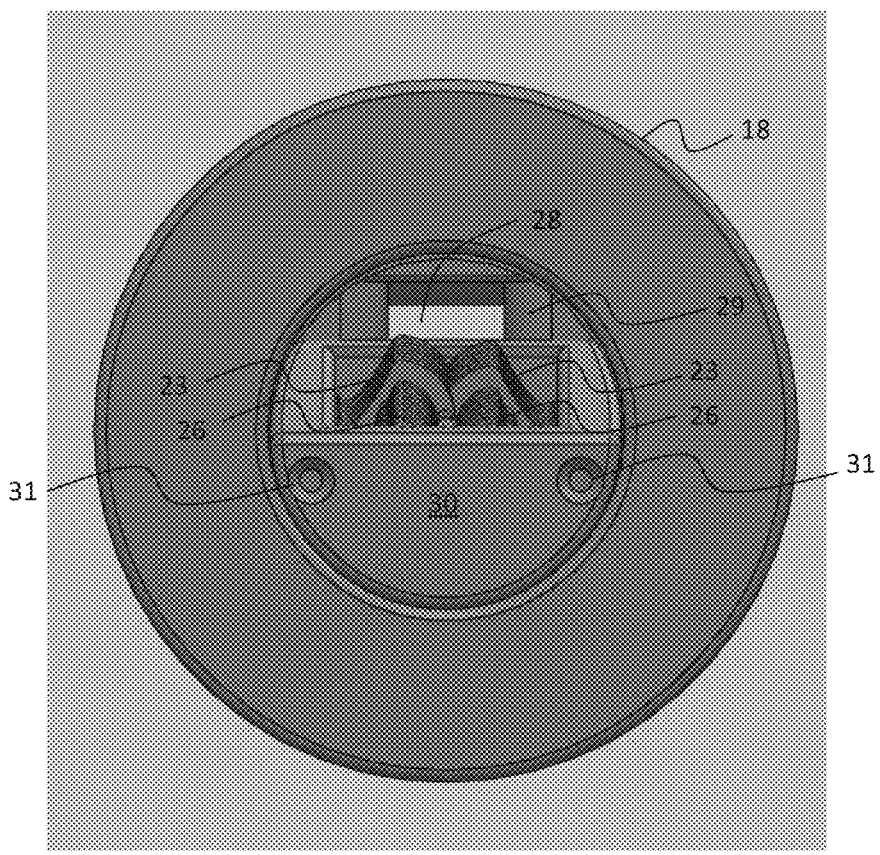
FIG. 6 is a front view of the embodiment of FIG. 1.
Figure 7:
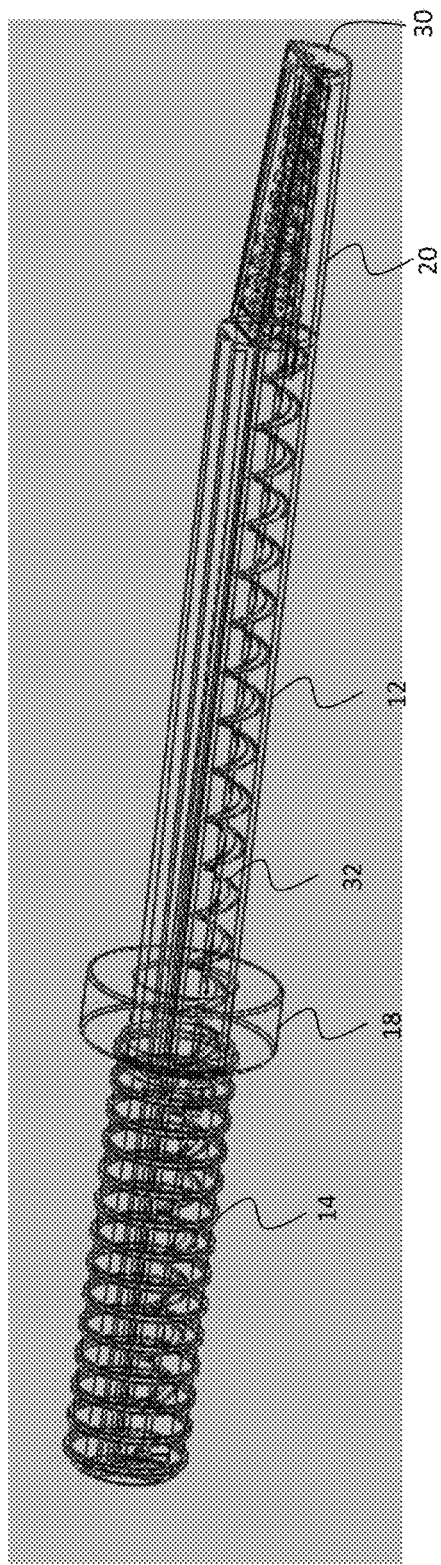
FIG. 7 is a perspective wire-frame view of the embodiment of FIG. 1.

Teeth 24 are disposed within window 25 of mouth 20 and may even protrude from window 25 to catch additional tissue masses within the body. As indicated in FIGS. 6 and 15, there can be two sets of opposing jaws 27a, 27b, each comprising drive shaft 26 and teeth 24. Teeth 24 of jaw 27a lie opposed to teeth 24 of jaw 27b.

Teeth 24 of jaws 27a interlock, or otherwise window, teeth 24 of jaw 27b, as clearly depicted in FIG. 15, such that teeth 24 that are adjacent to one another along a single jaw do not overlap each other. Further, teeth 24 of jaw 27a does not overlap with teeth 24 of jaw 27b since the teeth window each other. In other words, teeth 24 of jaw 27a are arranged in a staggered fashion with teeth 24 of jaw 27b. This allows tissue mass to be captured and torn/shredded, while still directing tissue mass into the interior of mouth 20 and ultimately to auger 32 for exiting morcellator 32.

Teeth 24 are separately mounted securely around corresponding drive shaft 26. Thus, when a motor and transmission gears (not shown) are activated, drive shafts 26 rotate simultaneously (typically counter-rotate), thus also rotating teeth 24 in a direction suitable for grasping and cutting tissue mass and pulling tissue mass into the interior of mouth 20 to auger 32. In certain embodiments, teeth 24 may be serrated or include a hook aspect, such that when teeth 24 rotate, tissue mass can be pinched and cut off. An example of a hook that may be used in conjunction with teeth 24 is indicated in FIG. 6 by the reference numeral 23. Hooks 23 can draw tissue into mouth 20 for cutting by teeth 24.

In an embodiment, each jaw 27a,27b may be made up of a single piece of material for ease of manufacture. For example, each of jaws 27a,27b may resemble a drill bit, where teeth 24 resemble the cutting edge/lands/margins of the drill bit with flute space disposed therebetween. The same principles would apply with teeth 24 of jaws 27a,27b being staggered.

As can be seen in FIG. 15, auger 32 lies beneath jaws 27a,27b and is fully enclosed within mouth 20 at the distal end of morcellator 20. Auger 32 extends proximally through sheath 12 and is enclosed within sheath 12. Auger support 33 can be positioned at the proximal end of auger 32 to hold auger 32 in place concentrically.

Figure 5:
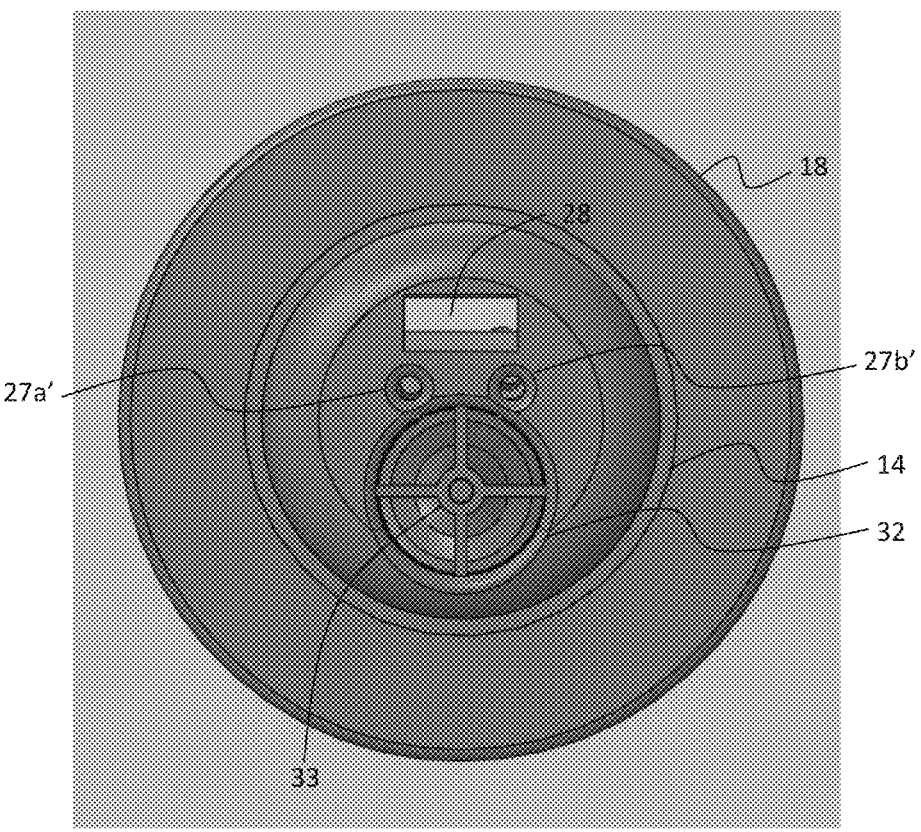
FIG. 5 is a back view of the embodiment of FIG. 1.

Jaws 27a,27b each extend adjacent to auger 32 proximally along interior 13 of the extent of sheath 12. Jaw 27a exits through port 27a' and jaw 27b exits through port 27b', as seen in FIGS. 5 and 12, to a system of motors and gears (not shown) that drive the rotation of jaws 27a,27b. Though it is shown that jaws 27a,27b and auger 32 are straight and parallel along sheath 12 until each exits handle 14 or handle guard 18, it is contemplated that jaws 27a,27b and auger 32 can exit morcellator 10 perpendicularly or otherwise at an angle if structurally and functionally feasible and more beneficial. For example, this may occur if the motor shaft and gears (not shown) require space within morcellator 10. Further, a collection structure (not shown) may be placed at the proximal end of morcellator 10, such that tissue mass directed by auger 32 toward the distal end of morcellator 10 can fall into and be collected by the collection structure. In this case, only jaws 27a,27b would have an angled extent and exit point out of morcellator 10.

Mouth 20 may be beveled when extending from sheath 12 with window 25 being angled relative to the line of axis of sheath 12, as indicated in FIGS. 1, 3, 4, 8, and 11. The angle provides greater surface area for teeth 24 to contact the tissue mass. It is contemplated that other embodiments of the current invention may include mouths that are not angled but rather lie along the same line of axis as sheath 12.

Figure 8:
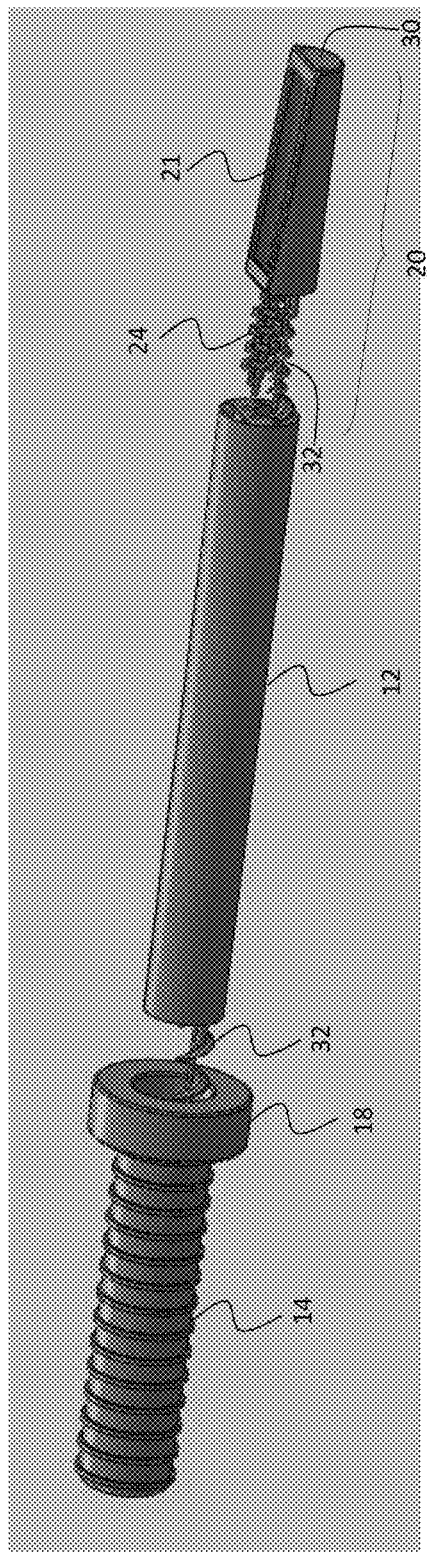
FIG. 8 is a perspective exploded view of the embodiment of FIG. 1.
Figure 9:
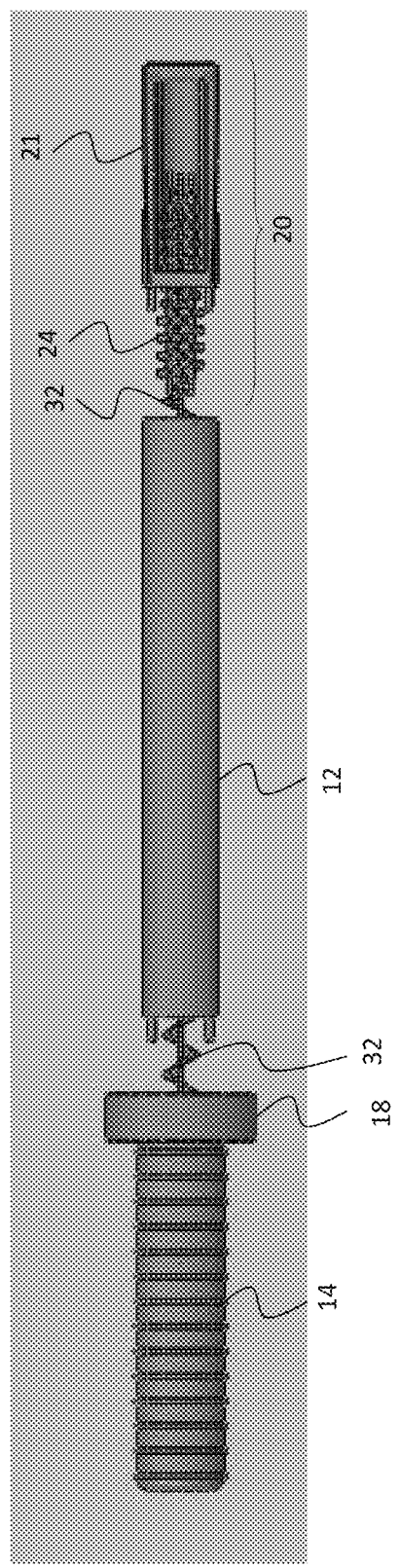
FIG. 9 is a top exploded view of the embodiment of FIG. 1.

Mouth 20 may terminate distally in safety tip 30, as seen in FIGS. 3, 6, and 8. Safety tip 30 is used to protect tissue masses in the body from morcellator 10. A user of morcellator 10 can push extraneous tissue out of the way of morcellator 10 prior to cutting the targeted tissue mass. Thus, the extraneous tissue can be protected from harm by safety tip 30.

As seen in FIG. 6, at the distal end of safety tip 30, fastening mechanisms 31 may be utilized to affix mouth 20 to sheath 12. Other conventional fastening mechanisms are contemplated by the current invention as well.

Conversely, on the proximal end of sheath 12, screw ports 39 may be utilized to fasten handle 14, handle guard 18, and/or machinery (e.g., motors, gears, etc.) (not shown) to sheath 12. Other conventional fastening mechanisms are contemplated by the current invention as well.

In practice, mouth 20 and a portion of sheath 12 of morcellator 10 is inserted into the body via a vagina or a laparoscopic port. Extraneous tissue can be pushed or manipulated by safety tip 30 to facilitate targeting of the target tissue mass by the user. Morcellator 10 can then be activated, thus rotating drive jaws 27a,27b (i.e., each drive shaft 26 and each corresponding set of teeth 24). As a tissue mass is mounted on or otherwise enters window 25 of mouth 20, teeth 24 grasp the tissue mass and cut the tissue mass, thus pulling the tissue mass inward toward auger 32. Thereafter, auger 32 directs the tissue mass proximally up sheath 12 and out of the body.

Figure 18:
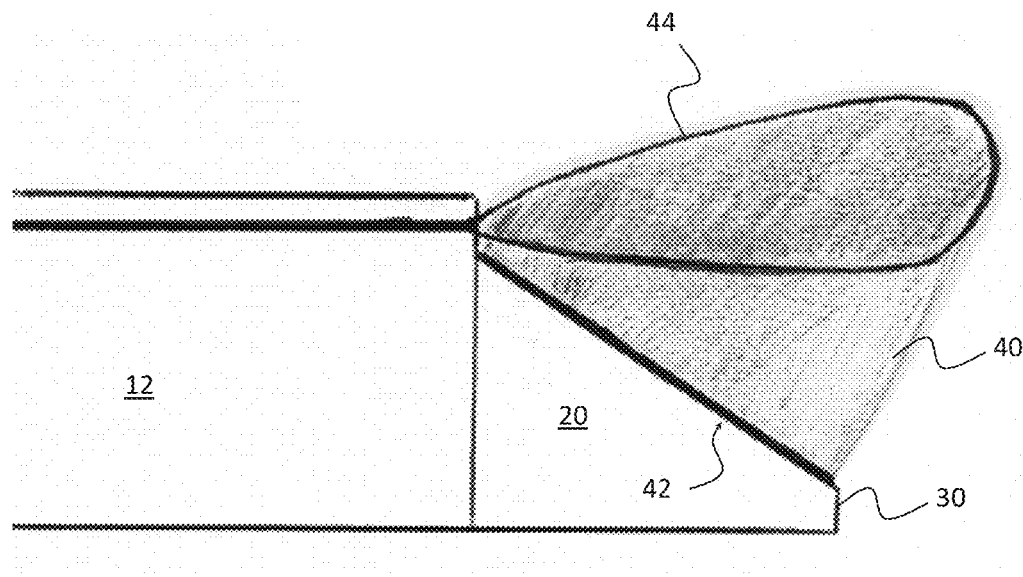
FIG. 18 is a schematic drawing of a cup assembly utilized in an embodiment of the current invention.
Figure 19:
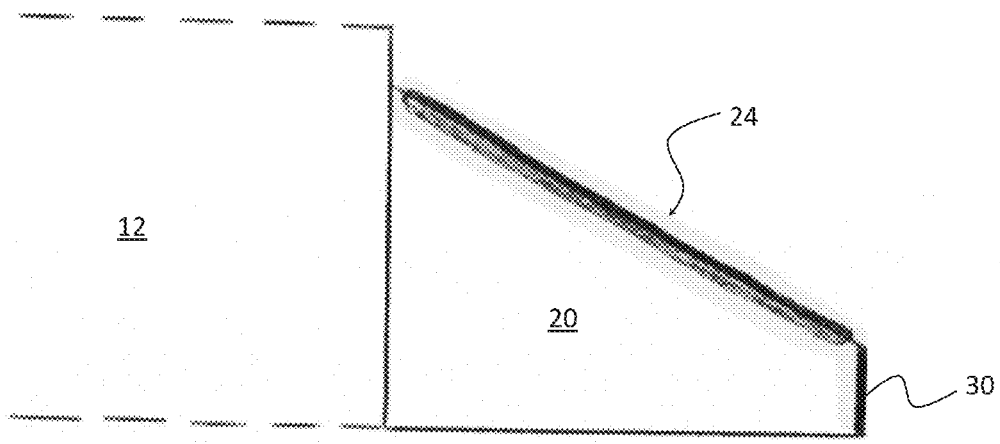
FIG. 19 is a schematic drawing of the blades guarded by a safety tip without the cup assembly of FIG. 18.

As depicted in FIG. 18, morcellator 12 may include cup assembly 40 for guiding or funneling tissue mass within the subject's body toward mouth 20 and placing the mass on mouth 20 for morcellation. The bottom closed edge of cup assembly 40 can line the edge of mouth casing 21 that forms the frame of window 25 leading into the interior of mouth 20, as can be seen at reference point 42 in FIG. 18. Thus, during insertion into the body, cup assembly 40 can be compressed and folded against the edge of mouth casing 21, such that the body of cup assembly 40 lies on top of mouth 20, thereby protecting the internal tissue masses from teeth 24. Subsequently, once mouth 20 is inserted into the body, cup assembly 40 can be expanded to guide a tissue mass into mouth 20.

To provide stability in the expanded position of cup assembly 40, as seen in FIG. 18, the open edge of cup assembly 40 can be lined with wire frame 44. Thus, in a compressed position, wire frame 44 would be folded inwardly and proximally to substantially cover mouth 20 and teeth 24. Upon insertion, wire frame 44 can be pushed into an expanded, open, and stable position, as indicated in FIG. 18.

A tissue mass can be placed in cup assembly 40 utilizing a laparoscopic grasper positioned through the subject's abdominal cavity or even possibly a grasper inserted through supplementary channel 28. Thus, cup assembly 40 holds the tissue mass in place as teeth 24 morcellates the mass and auger 32 directs the mass toward the exterior of the body. This prevents any tissue from remaining within the subject's body during or after the surgical procedure. Alternatively, cup assembly 40 can be utilized to scoop a tissue mass within the subject's body and stably guide the tissue mass to mouth 20 for morcellation by teeth 24 and subsequent removal via auger 32.

Cup assembly 40 typically is formed of a flexible material that facilitates the folding or manipulation of cup assembly 40 within mouth 20 or sheath 12 for subsequent deployment once inside the subject's body.

In an embodiment, as depicted in FIGS. 5, 6, and 12, cup assembly 40 can be folded or otherwise compressed within supplementary channel 28 during insertion of morcellator 10 into the subject's body. Alternatively, wire frame 44 may be pulled into supplementary channel 28 to ensure the cup assembly 40 is stretched taut over mouth 20 to maximize protection from teeth 24 and to minimize the size of morcellator 10 entering into the body.

Figure 16:
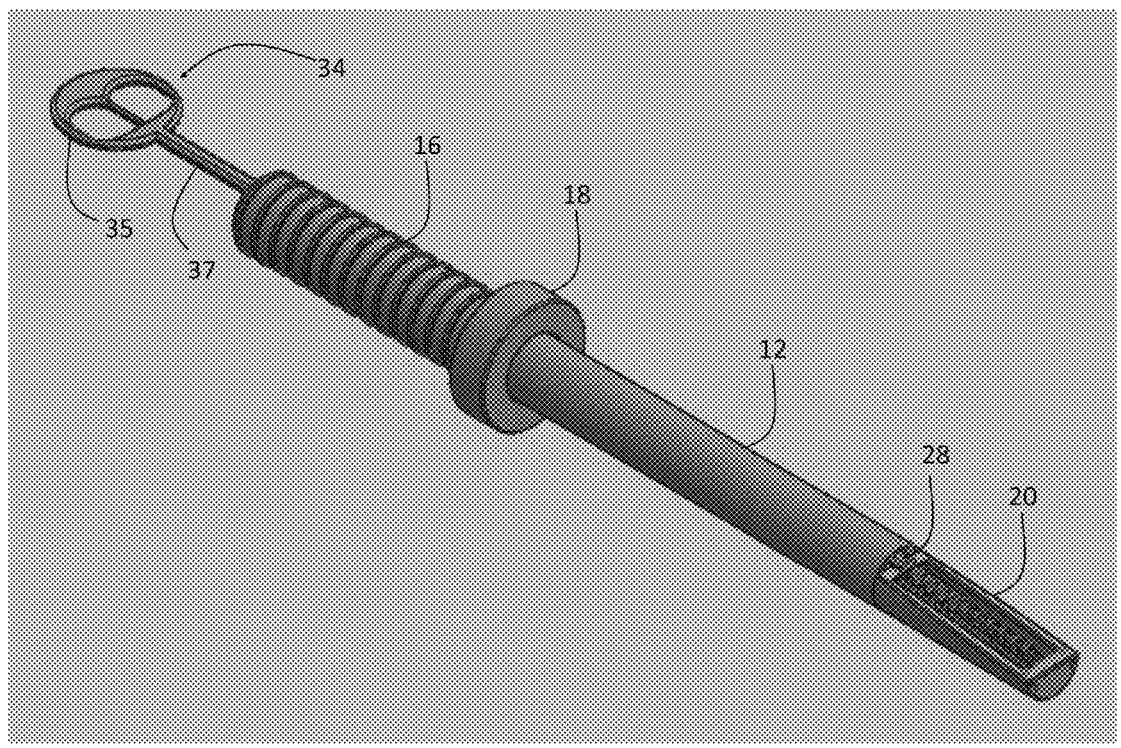
FIG. 16 is a perspective view of an embodiment of the current invention that utilizes a deploy apparatus for deploying a cup assembly into an expanded position.

As can be seen in FIG. 16, deploy apparatus 34 can be used to push or otherwise deploy cup assembly 40 from supplementary channel 28 (i.e., compressed position) into the expanded position seen in FIG. 18. Deploy apparatus 34 can include grip portion 35 and shank portion 37. The distal end of shank portion 37 may or may not be attached to the proximal end of wire frame 44 of cup assembly 40. Thus, it is contemplated that deploy apparatus 34 can be pushed distally to expand cup assembly 40 via expansion of wire frame 44, thus exposing teeth 24, and can be pulled proximally to compress cup assembly 40 within supplementary channel 28, thus covering teeth 24. During expansion and compression, the bottom edge of cup assembly 40 would remain attached to the outer edge of mouth casing 21.

Example 2

Figure 20:
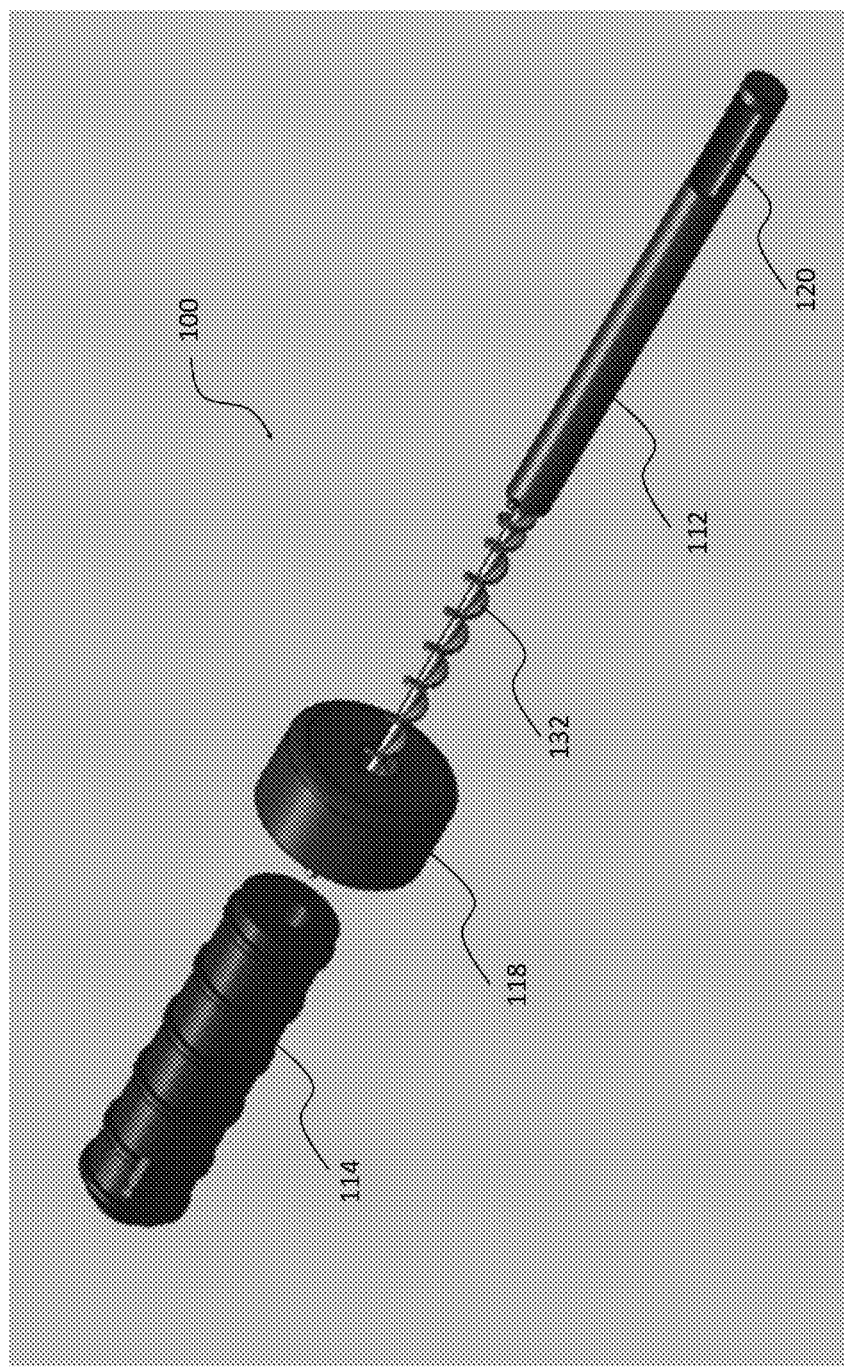
FIG. 20 is an exploded perspective view of an alternate embodiment of the current invention as may be utilized in traditional laparoscopic ports.

Referring to FIG. 20, morcellator 100 includes handle 114, hand guard 118, hollow sheath 112, and auger 132 for cutting and transportation of tissue masses. This embodiment of the invention is fabricated with mouth 120 having a longitudinal axis parallel to that of sheath 112, rather than being beveled or otherwise angled as in mouth 20 of Example 1 seen in FIG. 4.

Example 3

Figure 21:
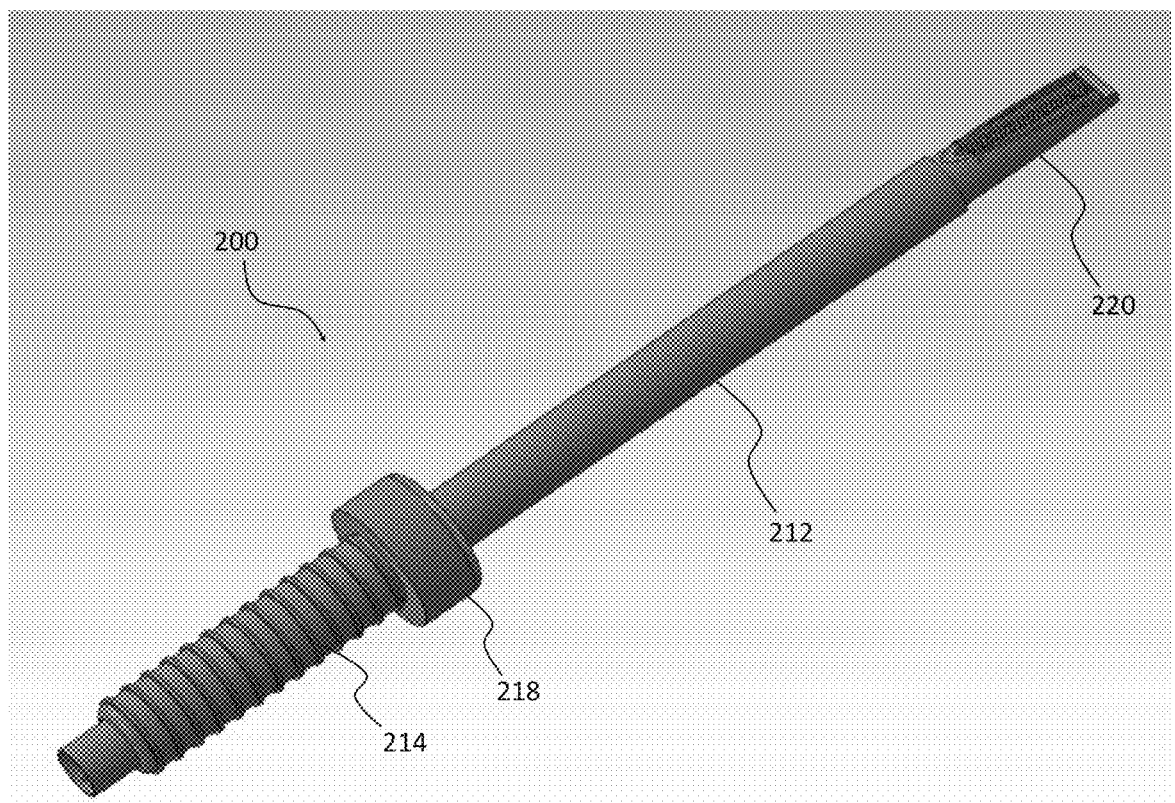
FIG. 21 is s perspective view of an alternate embodiment of the current invention utilizing a safety sheath.
Figure 22:
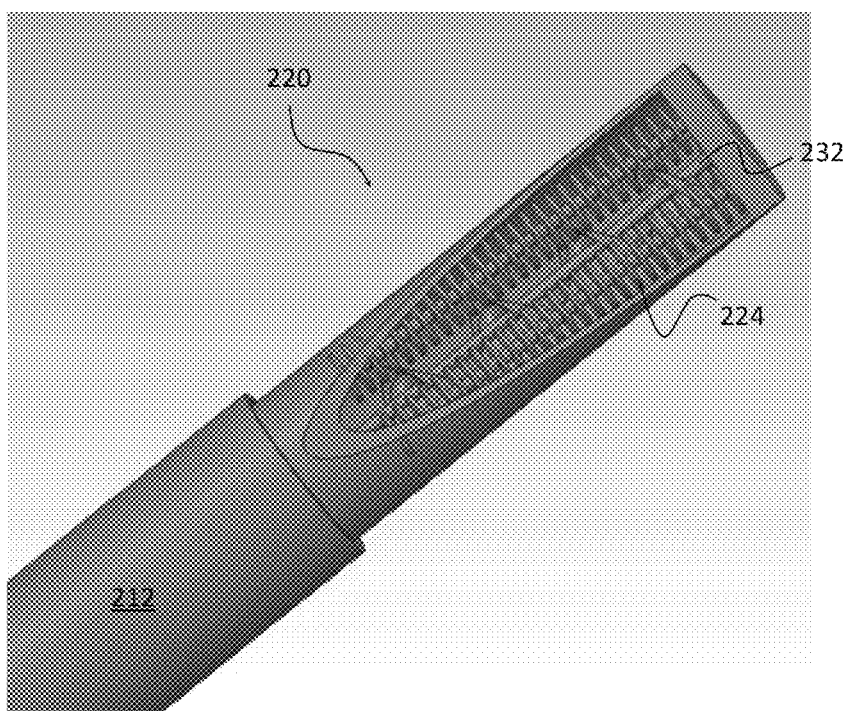
FIG. 22 is a perspective view of the distal end, in particular the mouth, of the embodiment FIG. 21.

Referring to FIGS. 21-22, this embodiment of the invention is adapted for the vaginal port and referred to by the reference numeral 212. This embodiment is similar to the one depicted in FIGS. 1-15, but further includes outer sheath 212 slidably positioned in outer relation to the inner sheath (not shown) disposed therewithin. As seen in FIG. 22, outer sheath 212 has a diameter larger than the inner sheath and is slidably disposed so as to slide over mouth 220 to safely cover rotating blades 224 and auger 232. The outer diameter of morcellator 200 with outer sheath 212 can be about 30 mm, and the diameter of inner sheath (not shown) can be about 22 mm. This embodiment would not include a cup assembly that covers the cutting blades, such as that seen in FIG. 18.

Outer sheath 212 is retractable and safely houses cutting blades 224 and auger 232 and can be used as an adjustable blade barrier to allow an increase or decrease in surface area of the amount of blades 224 exposed.

Methodologically, the sheath of the morcellator is inserted into the vaginal port. Once the proximal end of the sheath is inserted, the cutting blades are engaged in a rotational motion, and tissue contact may begin on the opening side of the sheath. Once cut, the cutting auger transports the tissue down the sheath to the distal end where it can be removed. While the blades and auger are in motion, the surgeon can adjust how much tissue that needs to be cut by moving the retractable sheath, thereby permitting an increase or decrease in the surface area on the exposed blades. This design reduces surgery time, while reducing surgical fatigue of the surgeon.

Example 4

Figure 23A:
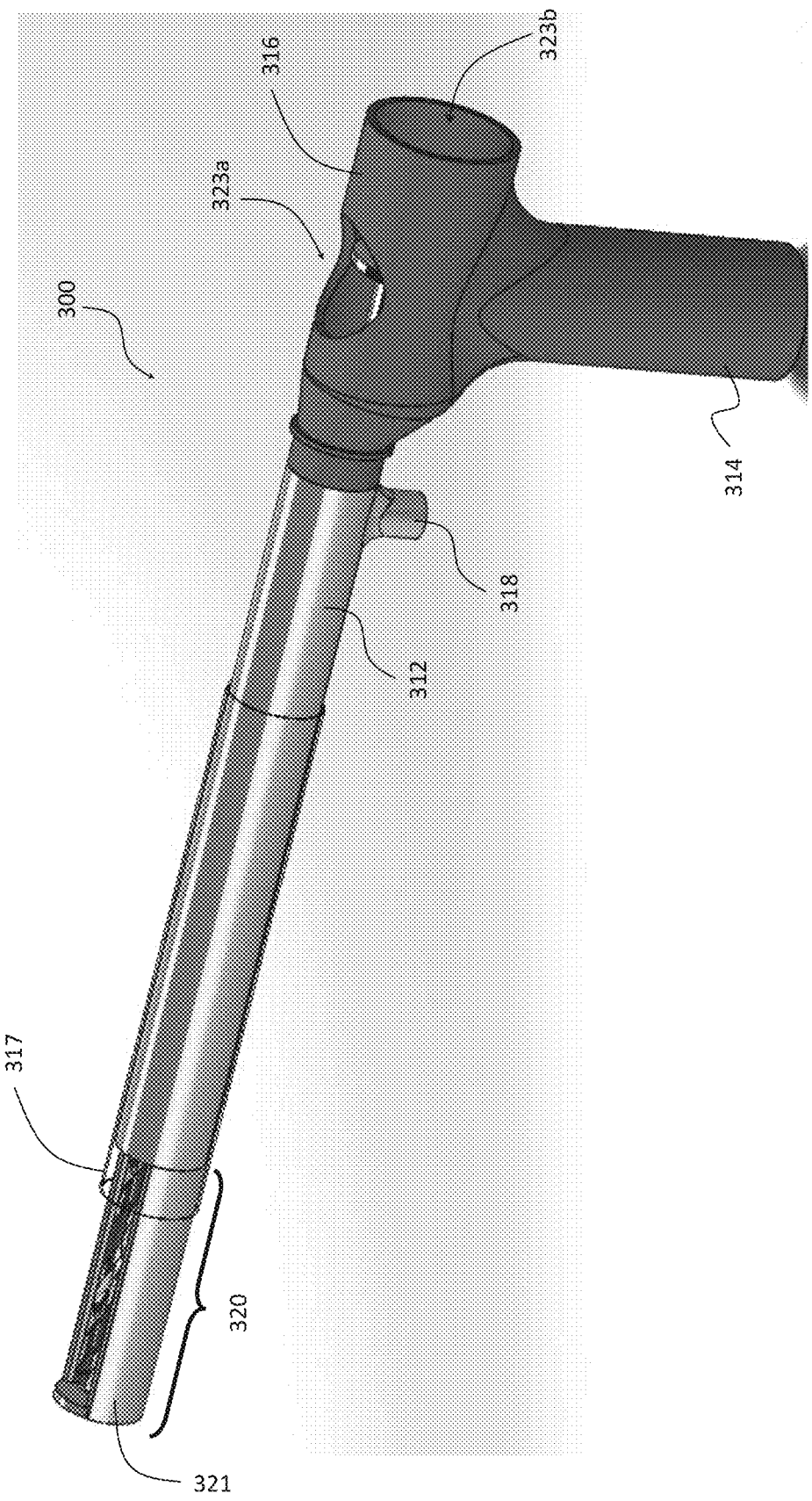
FIG. 23a is a perspective view of an alternative embodiment of the current invention.

FIGS. 23a-28b depict an alternative embodiment of the current invention. The morcellator of this embodiment is generally denoted by the reference numeral 300. FIG. 23a depicts the exterior aspects of morcellator 300. These exterior aspects include elongate sheath 312, handle 314, proximal body 316, mouth 320, and shoot 318. Morcellator 300 may further include optional bay sliding sheath assembly 317 that can slide over top mouth 320.

In this embodiment, handle 314 resembles a pistol grip and is positioned substantially perpendicular to the longitudinal axis of sheath 312. Proximal body 316 connects handle 314 to the proximal end of sheath 312.

Sheath 312 is straight and is intended to be inserted into a laparoscopic port or vagina of a subject. Mouth 320 extends from the distal end of sheath 312 and is concentric with sheath 312.

Shoot 318 is located at the proximal end of sheath 312 and can be positioned perpendicular to the axis of sheath 312. Shoot 318 acts as an exit point for the tissue mass when the tissue mass has been excised and traveled proximally through sheath 312. Upon exiting through shoot 318, the tissue mass can be collected or discarded.

Apertures 323a,323b on top of and at the rear of proximal body 316, respectively, are depicted for purposes of assembling morcellator 300.

Figure 23B:
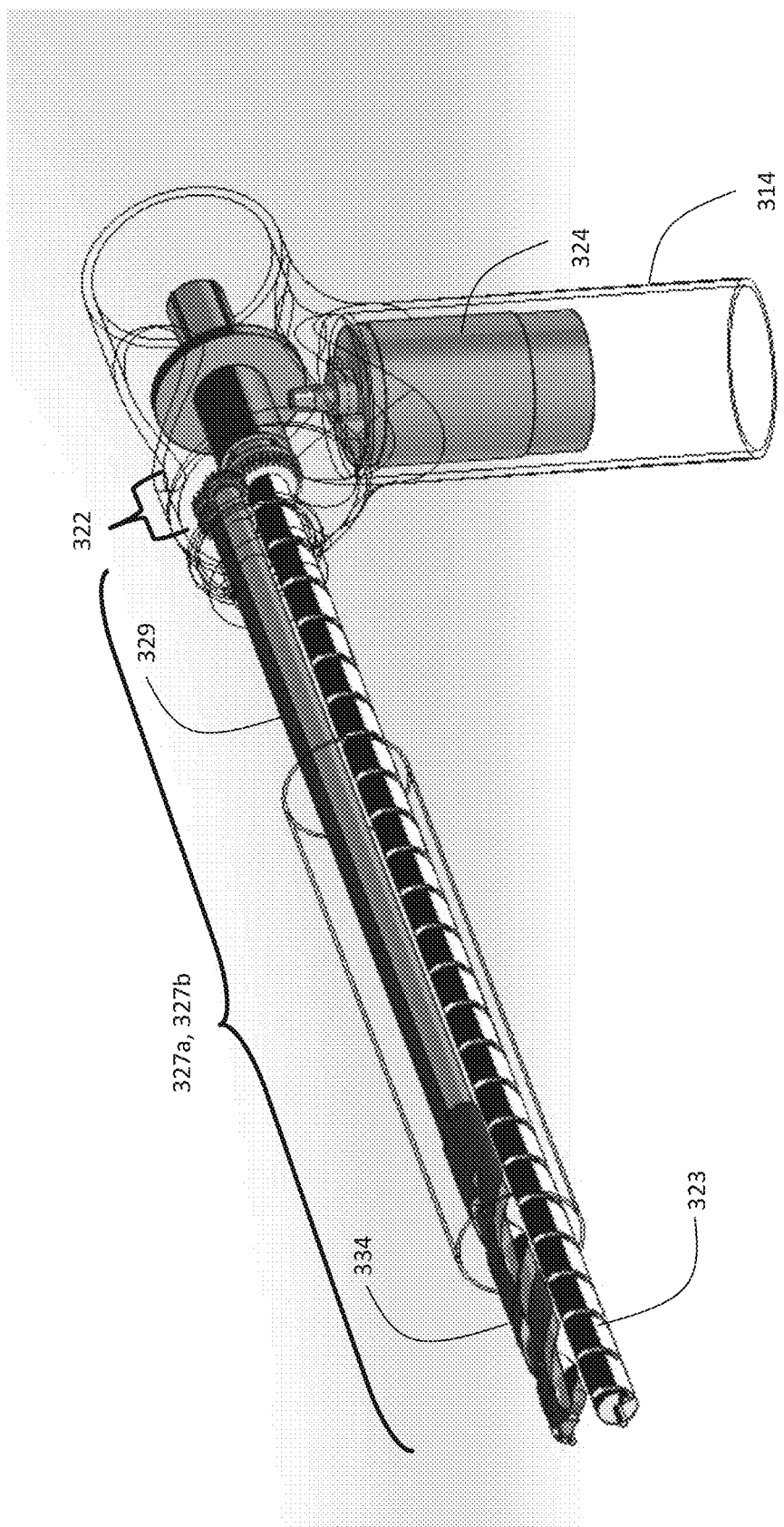
Figure 23C:
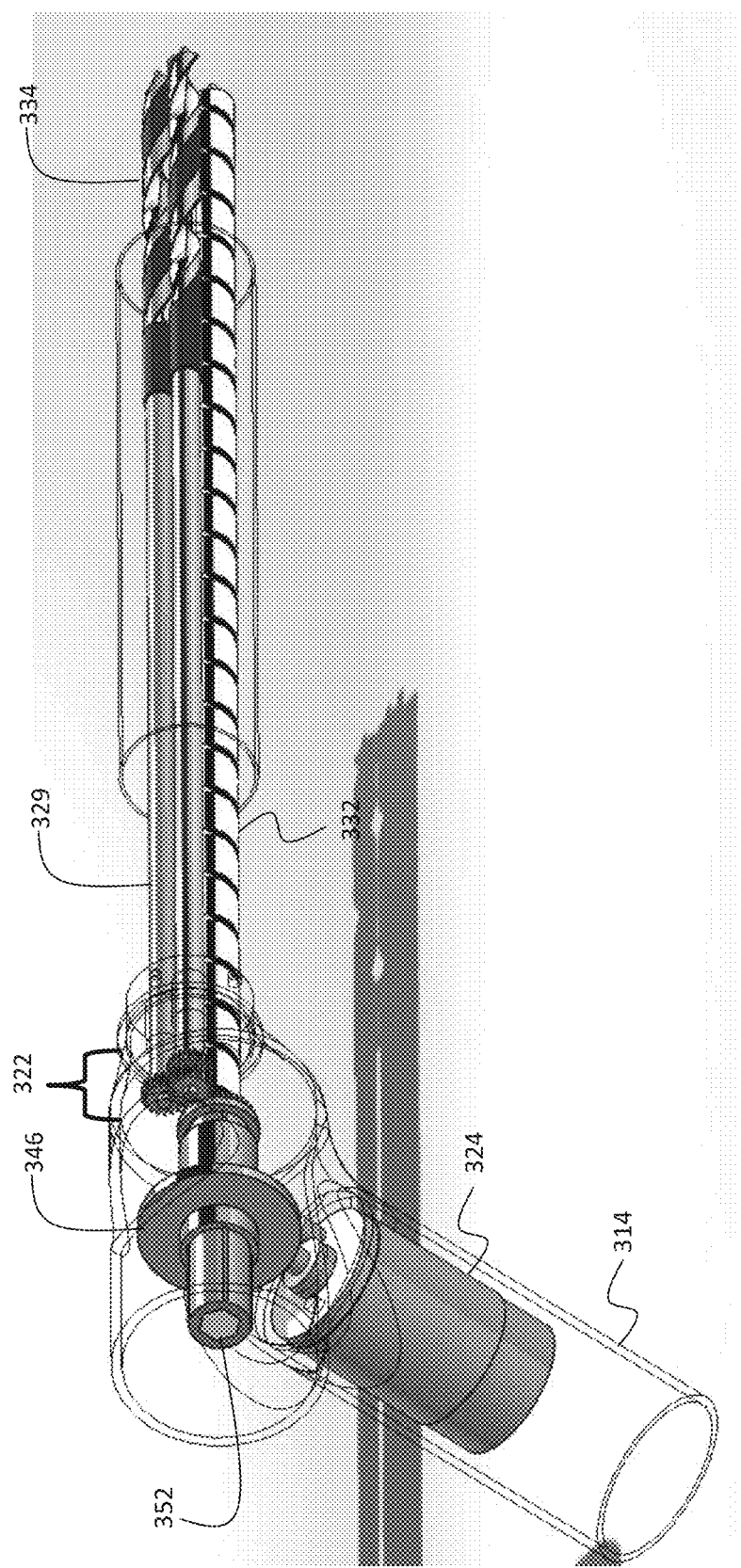
Figure 23D:
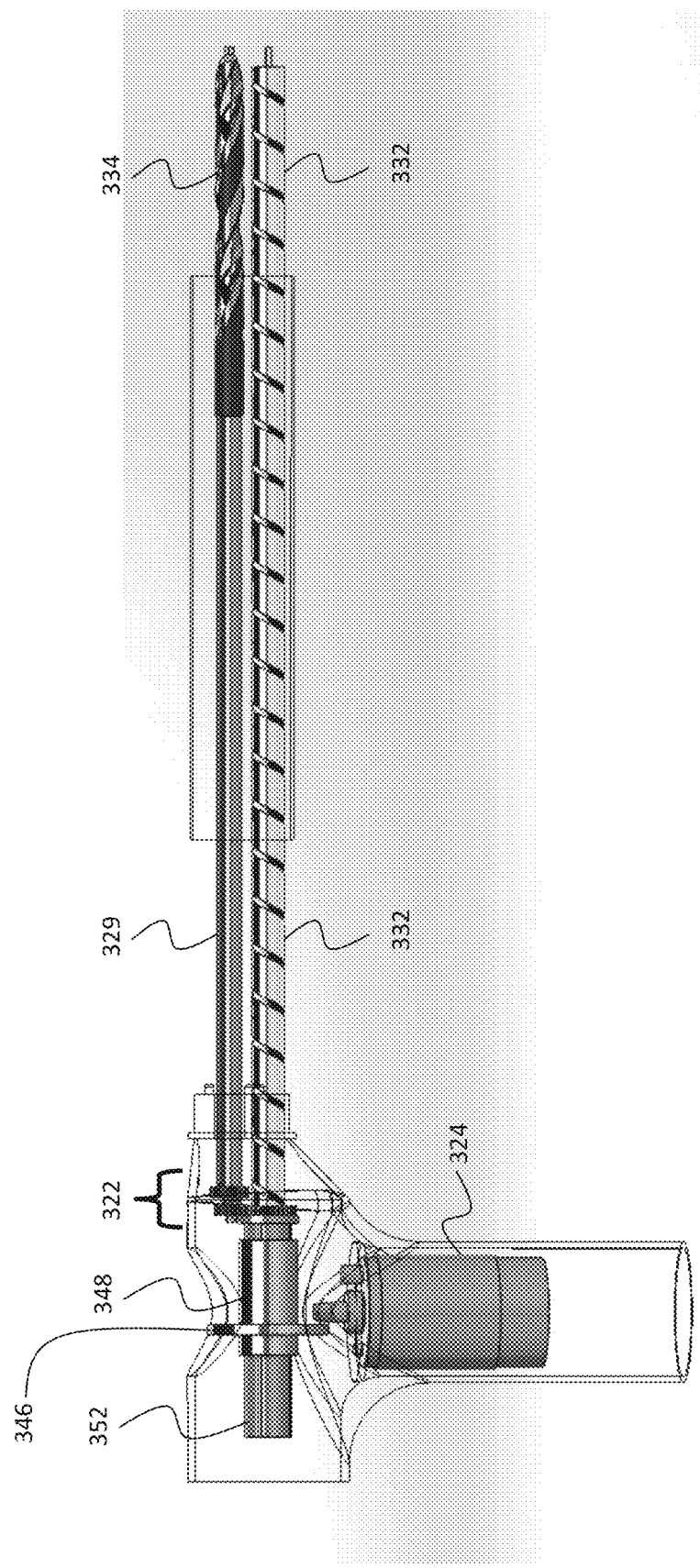

FIGS. 23b-23d are various angled wireframe views of morcellator 300 that depict the interior aspects of morcellator 300. These interior aspects include jaws 327a,327b, and further include auger 332, gear assembly 322, and motor unit 324. Each jaw 327a,327b is formed of straight or tapered shank 329 enclosed within sheath 312 and shredding body 334 enclosed within mouth 320 in communication with external environment via window 325. Each jaw 327a,327b may be formed of a single material and extend proximally in a straight manner along the length of sheath 312 and into mouth 320. As seen in FIG. 25c, shredding body 334 can be formed of a series of lands 336 (lands 336 of each jaw 327a,327b may interlock as described in Example 1) and flutes 338 that can cut tissue mass, though other forms of cutting or shredding teeth are contemplated by the current invention.

The proximal end of sheath 312 is coupled to gear assembly 322, which will become clearer as this specification continues.

Figure 24:
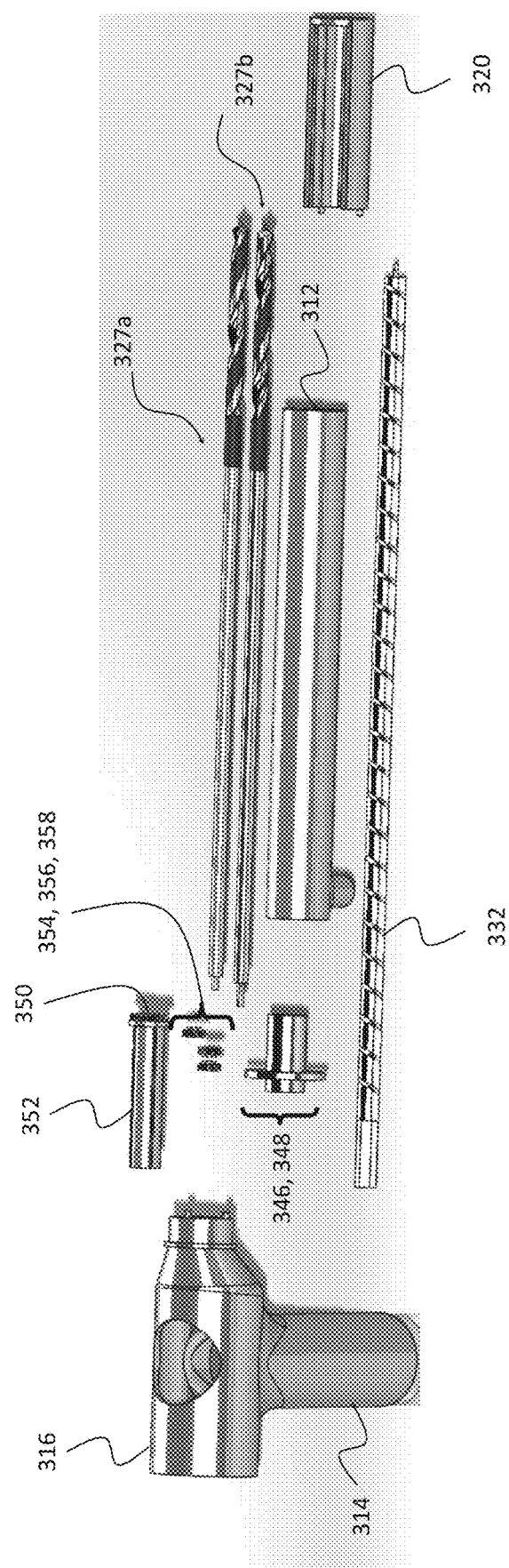
FIG. 24 depicts all parts used in the embodiment FIG. 23a as detached from one another.

Auger 332 has a substantially similar length as each jaw 327a,327b and is disposed beneath jaws 327a,327b and within mouth 320. Alternatively, auger 332 may have a length different from jaws 327a,327b, as seen in FIG. 24, but the distal end of jaws 327a,327b and auger 332 are similarly positioned within morcellator 300. Further, the term "beneath" is used relative to morcellator 300 being in an upright position, as seen in FIG. 23d, though morcellator 300 can be used in any position and at any suitable angle necessary for the surgical procedure. Further, auger 332 is substantially centered between jaws 327a,327b when positioned beneath jaws 327a,327b. Thus, when tissue mass is grasped and cut by shredding body 334 of each jaw 327a, 327b, the tissue mass is drawn between jaws 327a,327b and into auger 332. At this point, auger 332 rotates to guide the tissue mass proximally for exiting the body and morcellator 300.

The proximal end of auger 332 is coupled to gear assembly 322 as well, which will become clearer as this specification continues.

As indicated, the proximal ends of jaws 327a,327b and auger 332 are coupled to the distal side of gear assembly 322. The proximal side of gear assembly 322 is coupled to and is in mechanical communication with motor unit 324, which may include a battery or trigger mechanism (not shown). The battery and/or trigger mechanisms can be encapsulated by motor unit 324, can be an additional structure in handle 314, or can be a standalone box in electrical communication with motor unit 324.

FIG. 24 depicts several of the external and internal aspects or parts utilized in this embodiment of the current invention.

These aspects or parts include, but are not limited to, handle 314, proximal body 316, rotating disc 346 with keyed channel 348, driving spur gear 350 attached to the distal face of keyed shaft 352, driven spur gear 354, conjointly-rotating driving spur gear 356, driven spur gear 358, sheath 312, jaws 327a,327b, auger 332, and mouth 320. Each of these aspects are described herein.

Figure 25A:
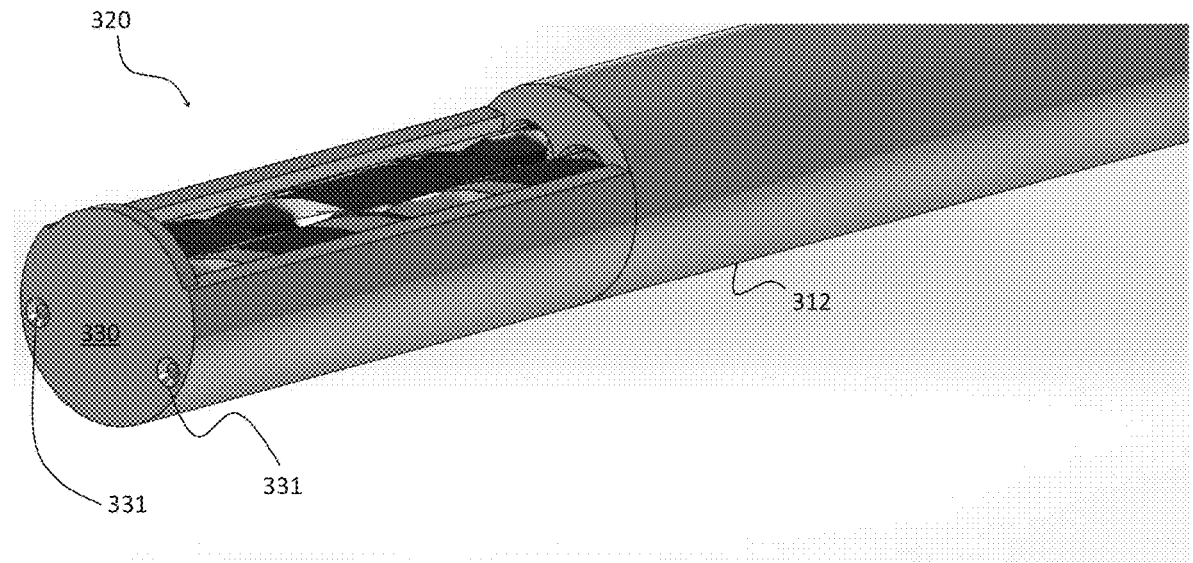
FIG. 25a is a front perspective view of the mouth of an embodiment of the current invention.
Figure 25B:
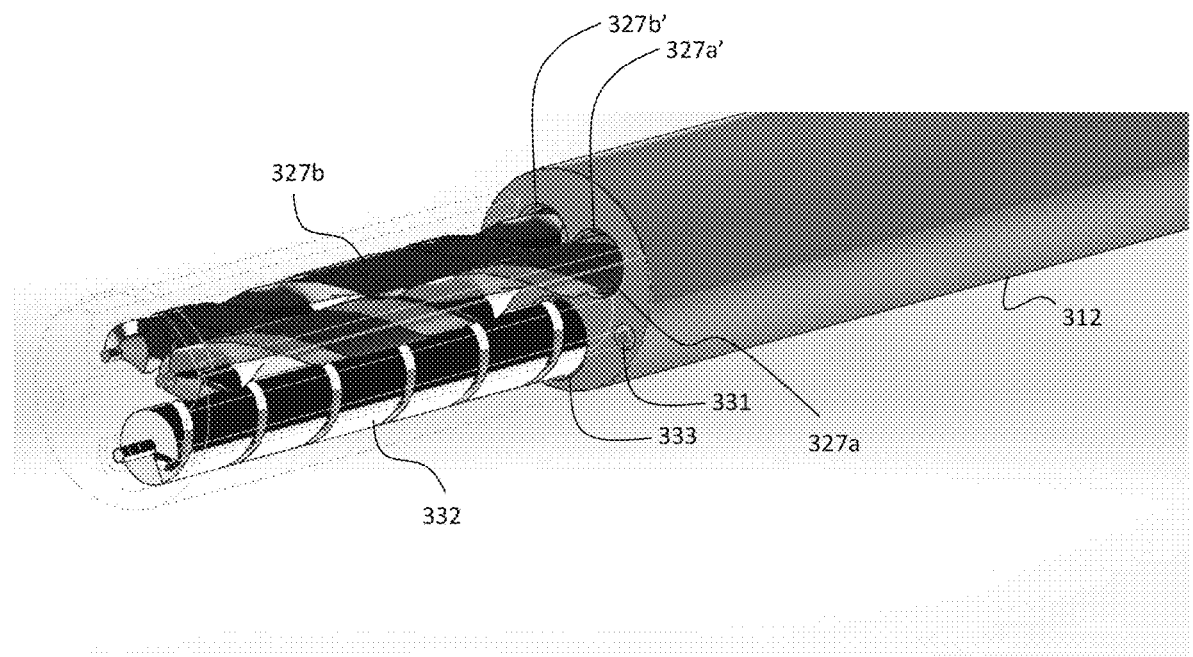
Figure 25C:
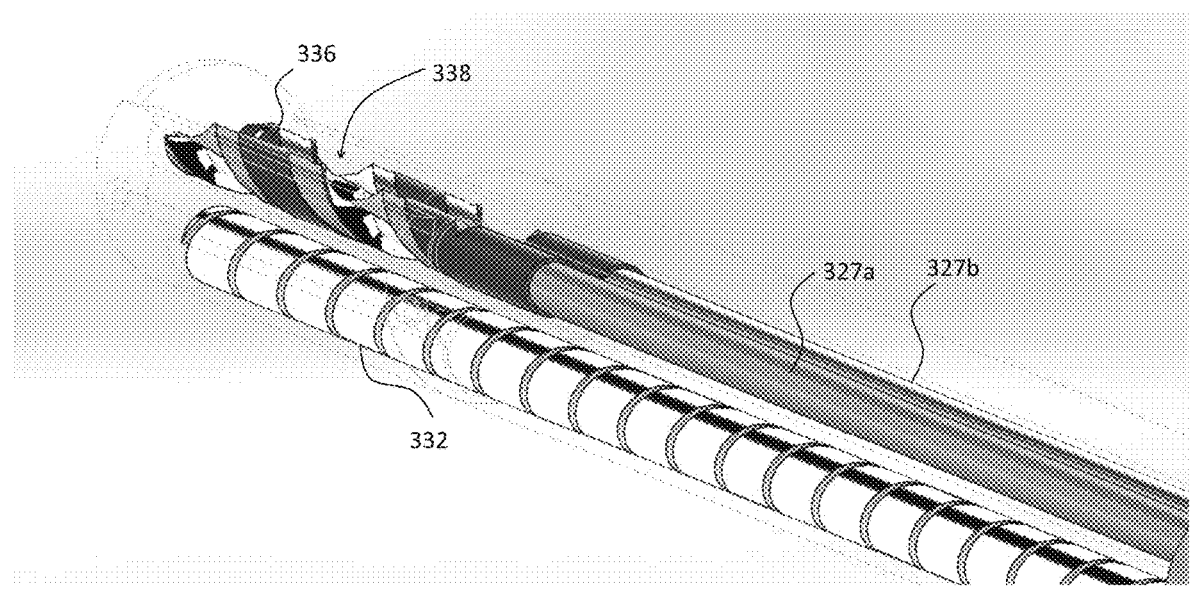

FIGS. 25a-25c depict mouth 320 and the distal end of sheath 312. As indicated particularly in FIG. 25b, the current invention contemplates that sheath 312 is not hollow; rather, a plurality of channels can be disposed along the extent of sheath 312, two (2) channels utilized for jaws 327a,327b and one (1) channel utilized for auger 332. Jaws 327a,327b exit the distal end of sheath 312 through ports 327a' and 327b', respectively, and auger 332 exits the distal end of sheath 312 through port 333. Once exiting sheath 312, jaws 327a,327b and auger 332 are contained within mouth 320. This aspect can further be seen in the exploded view of FIG. 26, as jaws 327a,327b and auger 332 enter their respective channels on the proximal end of sheath 312.

Referring to FIG. 25a, mouth 320 may further include safety tip 330 to protect extraneous tissue mass from morcellator 300. Safety tip 330 can be flat, as seen in FIG. 25a, or rounded, thus allowing the user to push or manipulate extraneous tissue when attempting to reach the targeted tissue mass.

As indicated in FIG. 25b, shredding body 334 of each jaw 327a,327b is contained within mouth 320 and possibly a portion of sheath 312, though it is contemplated that a majority of each jaw 327a,327b enclosed by sheath 312 is straight or tapered shank 329.

Fastening mechanisms 331 may be utilized on the distal end of mouth 320 to affix mouth 320 to sheath 312. Other conventional fastening mechanisms are contemplated by the current invention as well.

Figure 26:
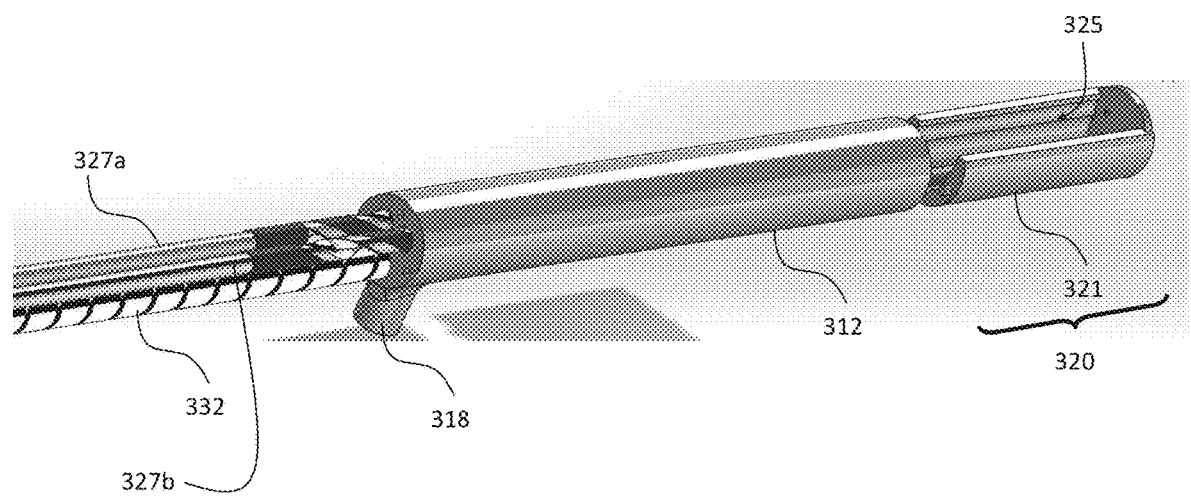

Mouth casing 321 forms the protective outer layer of mouth 320 on all sides other than window 325, as directed in FIGS. 25a and 26. Window 325 allows open communication between the hollow interior of mouth 320 and the external environment, though the current invention contemplates various mechanisms of covering window 325. Examples of these mechanisms will become clear as this specification continues.

FIG. 25c shows more clearly the positioning of auger 332 relative to jaws 327a,327b. Auger 332 is positioned beneath jaws 327a,327b and substantially centered between jaws 327a,327b.

Figure 27:
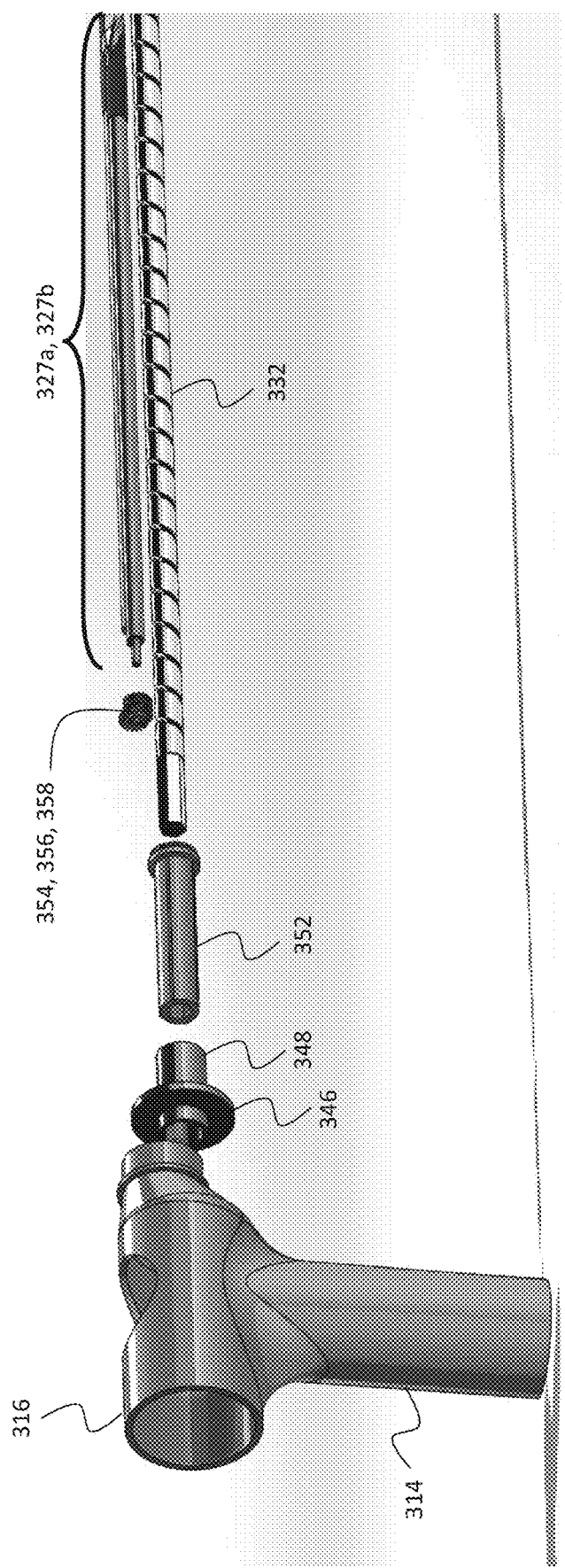
FIG. 27 is a rear exploded view of an embodiment of the current invention.

FIG. 27 is an exploded view of the proximal end of morcellator 10. Rotating disc 346 with keyed channel 348 is positioned within proximal body 316 above perpendicular handle 314, which encloses at least a portion of the motor unit (not shown in this figure). Rotating disc structure 346,348 is coupled to the motor unit, which, when activated, rotates rotating disc structure 346,348. Keyed shaft 352 is keyed into channel 348 of rotating disc structure 346,348. Thus, when rotating disc structure 346,348 rotates, keyed shaft 352 rotates as well.

Driving spur gear 350 is securely attached to the distal end of keyed shaft 352, such that when keyed shaft 352 rotates, driving spur gear 350 rotates as well. Spur gears 354,356, 358 are meshably engaged with driving spur gear 350 and/or with each other in a manner that when rotating disc structure 346,348 rotates, gears 354,356,358 will rotate as well. The purpose of this arrangement is so that jaws 327a,327b and auger 332 will rotate simultaneously. The proximal end of auger 332 is securely attached to driving spur gear 350 in a conventional manner. Jaws 327a,327b are securely attached to conjointly rotating driving spur gear 356 and driven spur gear 358, respectively, in a conventional manner. Considering the functionality desired of simultaneous rotation of jaws 327a,327b and auger 332, any suitable arrangement of gears in gear assembly 322 is envisioned.

Figure 28A:
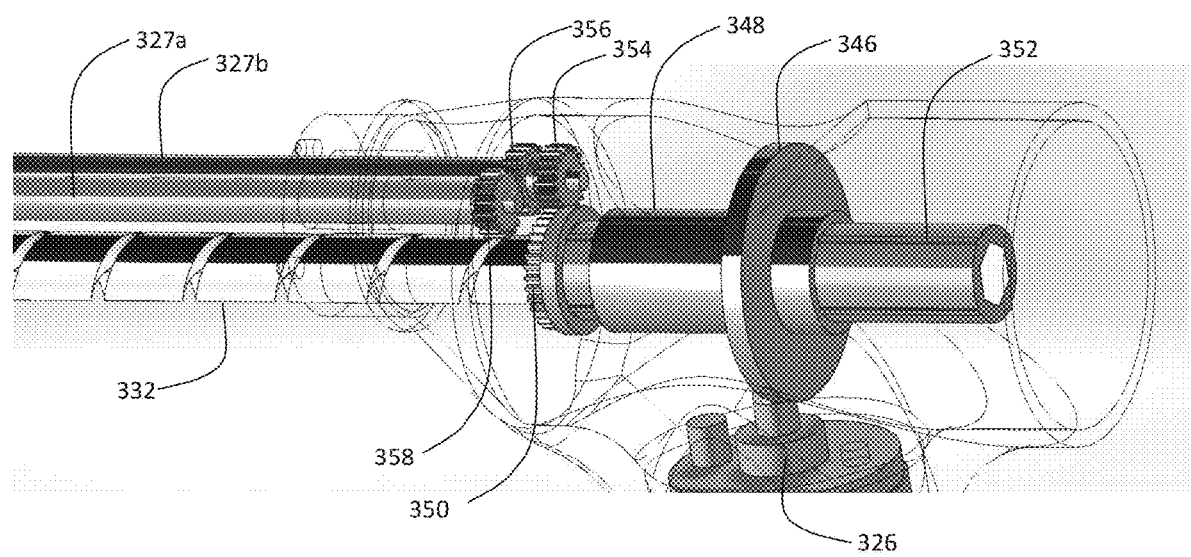
FIG. 28a is a rear perspective, close-up wireframe view of a gear assembly utilized in an embodiment of the current invention.
Figure 28B:
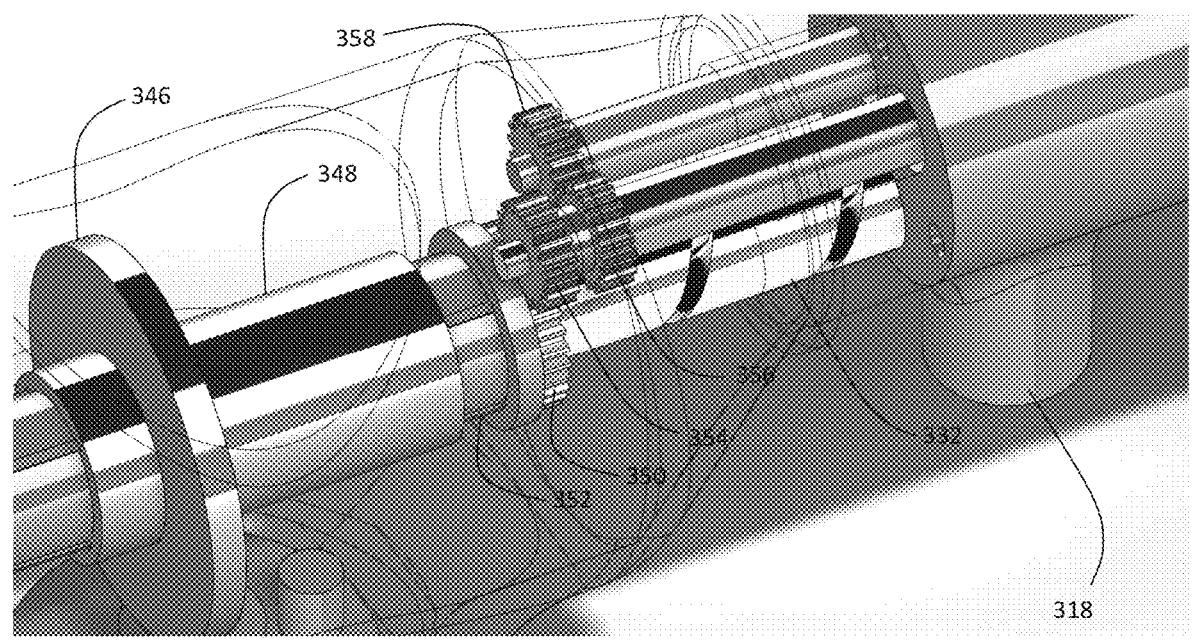

In an embodiment, as depicted in FIGS. 28a and 28b, gear assembly 322 includes rotating disc 346 with keyed channel 348, keyed shaft 352, driving spur gear 350, driven spur gear 354, conjointly-rotating driving spur gear 356, and driven spur gear 358. Keyed shaft 352 aligns with and is inserted through keyed channel 348, such that rotation of rotating disc 346 rotates keyed shaft 352 as well. Driving spur gear 350 is securely attached to the distal end of keyed shaft 352. As seen in FIG. 28a, the proximal end of keyed shaft 352 is tool-engageable. Thus, keyed shaft 352 can be rotated manually or electrically through aperture 323b, if desired or needed.

Still referring to FIGS. 28a and 28b, driving spur gear 350 is meshably engaged with driven spur gear 354. Conjointly-rotating driving spur gear 356 is coupled to driven spur gear 354 in spaced concentric relation to driven spur gear 354 and distal to driven spur gear 354. Conjointly-rotating driving spur gear 356 is meshably engaged with driven spur gear 358. Thus, although conjointly-rotating spur gear 356 is driven by rotation of driving spur gear 350, conjointly-rotating spur gear 356 becomes a driving gear by actuating the rotation of driven spur gear 358.

The proximal end of auger 332 is securely coupled to driving spur gear 350. The proximal end of jaw 327b is securely coupled to conjointly-rotating driving spur gear 356. The proximal end of jaw 327a is securely coupled to driven spur gear 358.

In an alternative embodiment, a sun and planet gear system may be utilized, thus eliminating conjointly-rotating driving spur gear 356 by meshably engaging driven spur gear 358 with driving spur gear 350. While the ultimate function of simultaneous rotation of jaws 327a,327b and auger 332 should be achieved, the gear assembly used can be altered, depending on the needs of the user.

As indicated in FIG. 28a, motor unit 324 is positioned within handle 314 perpendicular to gear assembly 322. Motor unit 324 is electrically coupled to gear assembly 322 via power takeoff shaft 326. Motor unit 324 is capable of activating, deactivating, and controlling the rotation of gear assembly 322. Any conventional methodology of controlling the rotation of rotating disc 346 and/or gear assembly 322 is envisioned by the current invention. For example, a worm gear (not shown) may be utilized, but other suitable mechanisms are available as well.

Methodologically, motor unit 324 is activated to initiate rotation of rotating disc 346, which rotates keyed shaft 352. Rotation of keyed shaft 352 rotates driving spur gear 350, which in turn rotates auger 332, driven spur gear 354, and conjointly-rotating driving spur gear 356. Rotation of conjointly-rotating driving spur gear 356 rotates jaw 327b and driven spur gear 358. Rotation of driven spur gear 358 rotates jaw 327a. Thus, activation of motor unit 324 results in simultaneous rotation of auger 332, jaw 327b, and jaw 327a.

The current invention contemplates a variety of mechanisms that can cover or fill window 325 while morcellator 300 is not in use or during insertion of morcellator 300 into the subject's body. Window 325 can remain covered or filled until just prior to cutting by shredding body 334 of each jaw 327a,327b. At this point, the cover can be removed to expose auger 332 and shredding body 334 of each jaw 327a,327b to the internal tissue masses. Various non-limiting mechanisms for covering window 325 are provided in Examples 5-8.

Example 5

Figure 29A:
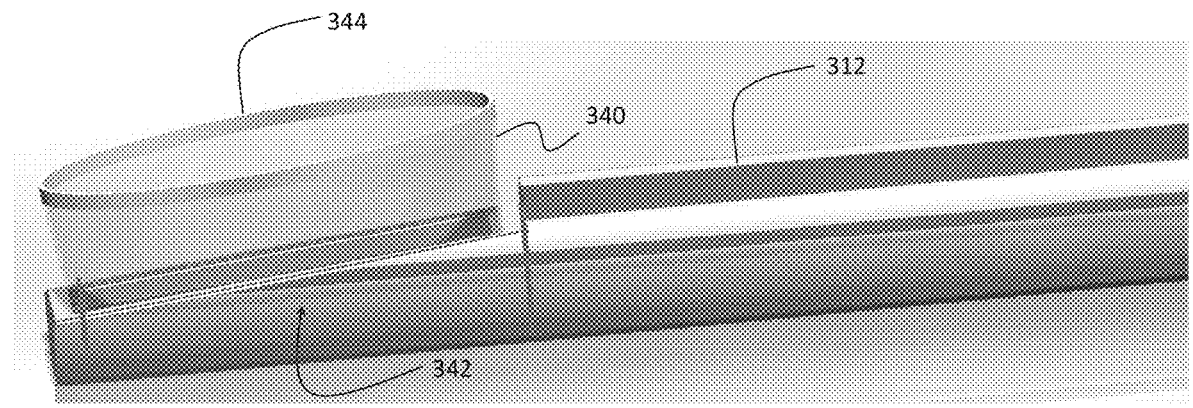
FIG. 29a is a side perspective view of a cup assembly utilized in an embodiment of the current invention.
Figure 29B:
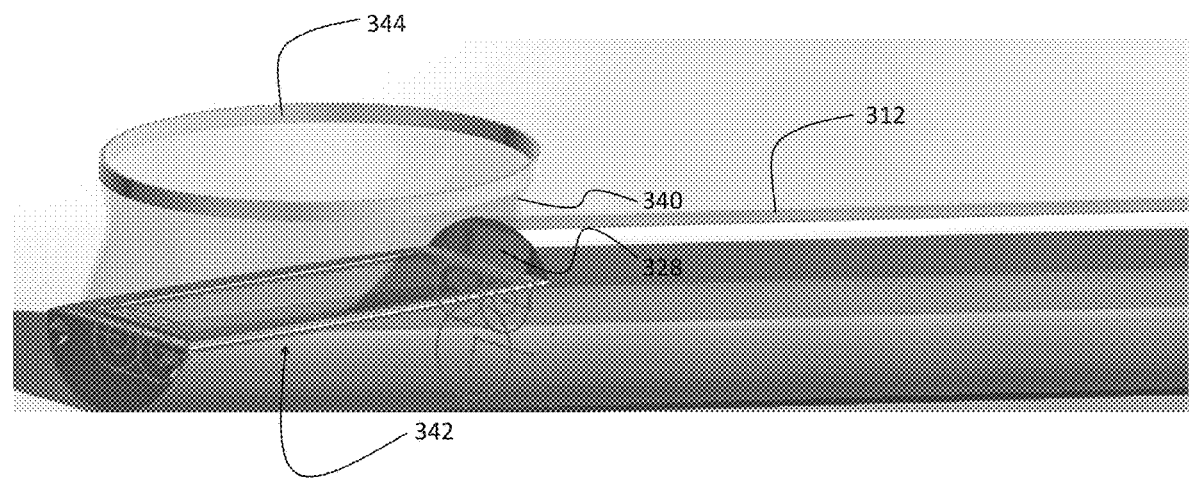

FIGS. 29a and 29b illustrate an optional addition to morcellator 300, said addition being cup assembly 340 with supplementary channel 328 extending along the extent of sheath 312 for enclosing and deploying cup assembly 340. As seen more clearly in FIG. 29b, the bottom edge of cup assembly 340 is attached to mouth 320, for example by being attached to mouth casing 321 or the outer edges of window 325. In particular, this can be seen in FIG. 29b at reference numeral 342.

Cup assembly 340 has a compressed position and an expanded position. In a compressed position, cup assembly 340 would be enclosed within supplementary channel 328, though cup assembly 340 would provide a coverage over window 325 in the compressed position because of the attachment of the bottom edge of cup assembly 340 to mouth 320. Prior to excising of tissue mass, cup assembly 340 can be deployed into the expanded position seen in FIGS. 29a and 29b. Cup assembly 340 can scoop or otherwise direct tissue mass toward mouth 320 for morcellation by shredding body 334 and transportation (and further morcellation) by auger 332.

Cup assembly 340 includes wire frame 344 along its top edge when in its expanded position. Wire frame 344 stabilizes cup assembly 340 in an upright position.

Example 6

Figure 30A:
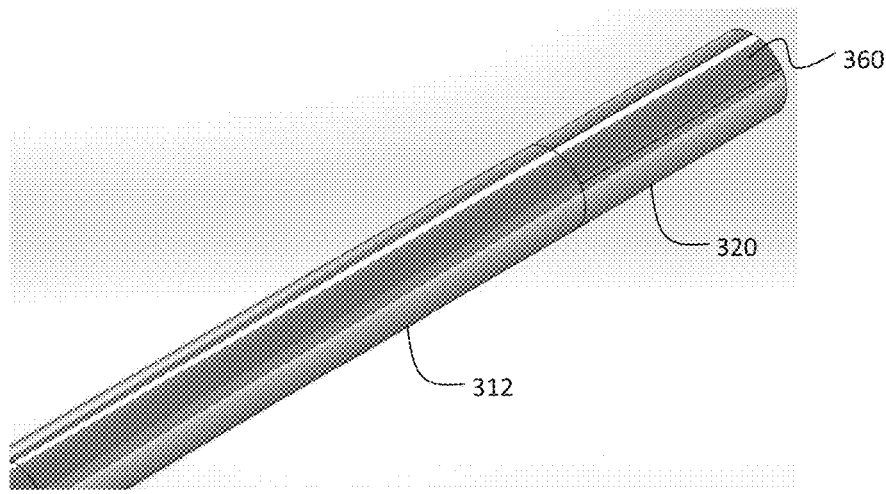
FIG. 30a is a perspective view of a bay door assembly utilized in an embodiment of the current invention for covering the mouth of the morcellator, where the bay door assembly is in a closed position.
Figure 30B:
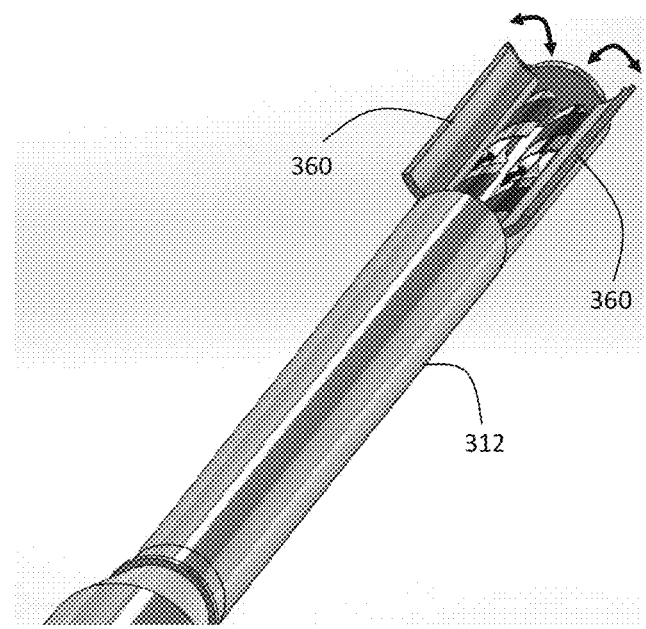
FIG. 30b is a perspective view of the bay door assembly of FIG. 30a in an open position.
Figure 30C:
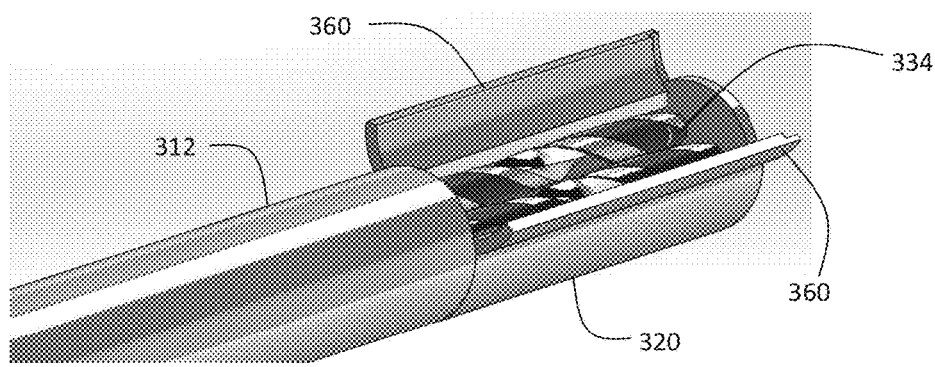
FIG. 30c is a rear perspective view of the bay door assembly of FIG. 30a in an open position.

FIGS. 30a-30c depict a mechanism for covering window 325 using bay doors 360. FIG. 30a shows mouth 320 when bay doors 360 are closed, whereas FIGS. 30b and 30c show mouth 320 when bay doors 360 are open in the direction of the arrows to expose shredding body 334 of each jaw 327a,327b. Bay doors 360 may be a single door (not shown) or multiple figures as seen in FIGS. 30a-30c. Further, bay doors 360 can open in any direction, for example transversely (not shown) or longitudinally as seen in FIGS. 30a-30c. A triggering mechanism (not shown) would be included in proximity to handle 314 or proximal body 316 for opening and closing bay doors 360.

Methodologically, morcellator 300 would be inserted into the subject's body with bay doors 360 closed, as in FIG. 30a. Subsequently, prior to contacting the targeted tissue mass, bay doors 360 can be opened using triggering mechanism (not shown), thus exposing the tissue mass to the shredding body of each jaw 327a,327b for morcellation.

Example 7

Figure 31A:
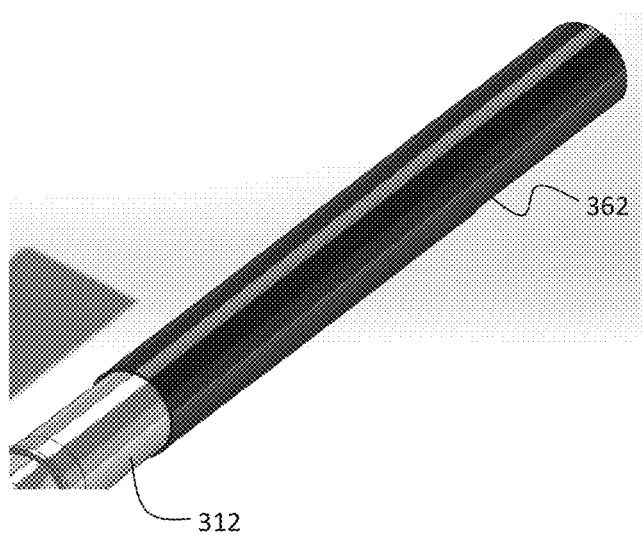
FIG. 31a is a perspective view of a bay rotating sheath assembly utilized in an embodiment of the current invention for covering the mouth of the morcellator, where the bay rotating sheath assembly is in a closed position.
Figure 31B:
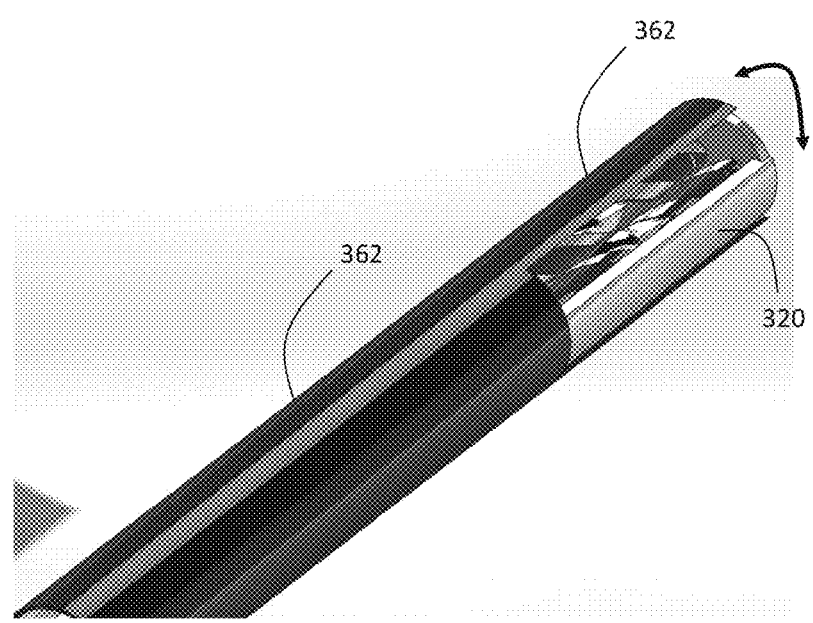
FIG. 31b is a perspective view of the bay rotating sheath assembly of FIG. 31a in a half-open position.
Figure 31C:
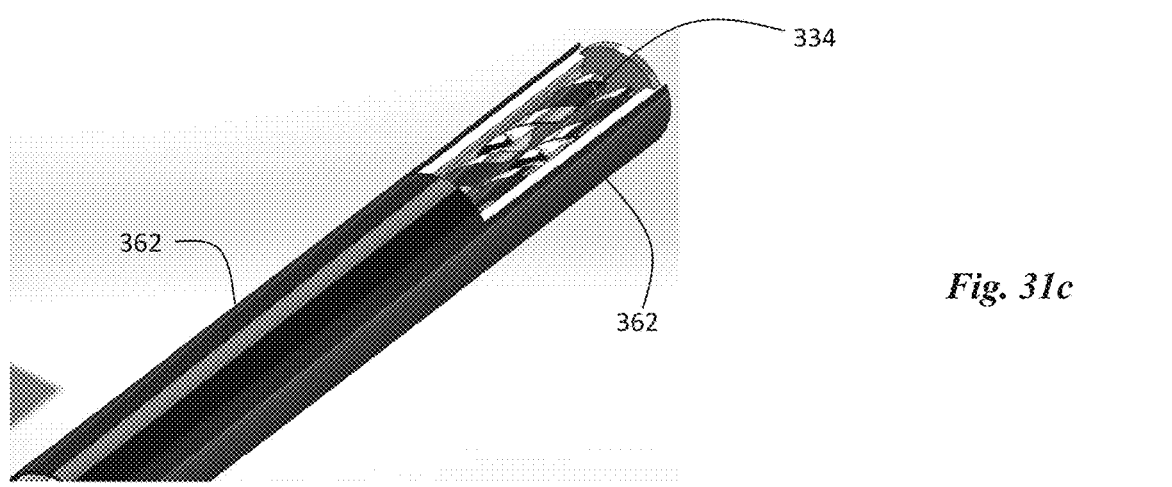
FIG. 31c is a perspective view of the bay rotating sheath assembly of FIG. 31a in an open position.

FIGS. 31a-31c depict a mechanism for covering window 325 using bay rotating outer sheath 362. Bay rotating outer sheath 362 has a cutout in the shape of window 325. FIG. 31a shows mouth 320 when bay rotating outer sheath 362 is rotated to completely cover window 325. FIG. 31b depicts rotation of bay rotating outer sheath 362 in the direction of the arrow to expose half of window 325. FIG. 31c depicts window 325 when bay rotating outer sheath 362 has been fully rotated in the direction of the arrow such that the cut out of outer sheath 362 is aligned with window 325, thus fully exposing window 325. Bay rotating outer sheath 362 may have any suitable length that facilitates its rotation. This rotation may be achieved manually if the length extends to proximal body 316 (i.e., outside of the body), or it may be done automatically upon activating a trigger mechanism (not shown) in a conventional manner.

Methodologically, morcellator 300 would be inserted into the subject's body with bay rotating outer sheath 362 rotated to close off window 325, as in FIG. 31a. Subsequently, prior to contacting the targeted tissue mass, bay rotating outer sheath 362 can be rotated to expose as much of shredding body as desired by the user. For example, if the user desires to morcellate only a relatively small piece of tissue, the user may desire to open only half of window 325, as in FIG. 31b. Alternatively, the user may desire to expose all of shredding body by rotating the cutout of bay rotating outer sheath 362 into alignment with window 325.

Example 8

Figure 32A:
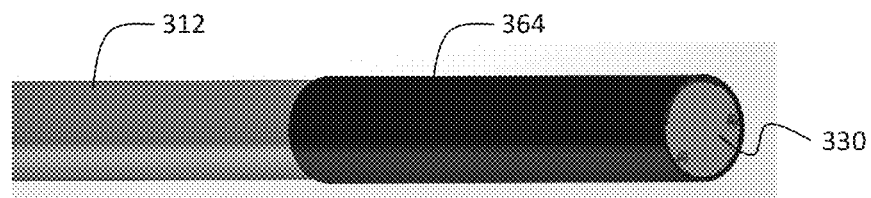
FIG. 32a is a perspective view of a bay sliding sheath assembly utilized in an embodiment of the current invention for covering the mouth of the morcellator, where the bay sliding sheath assembly is in a closed position.
Figure 32B:
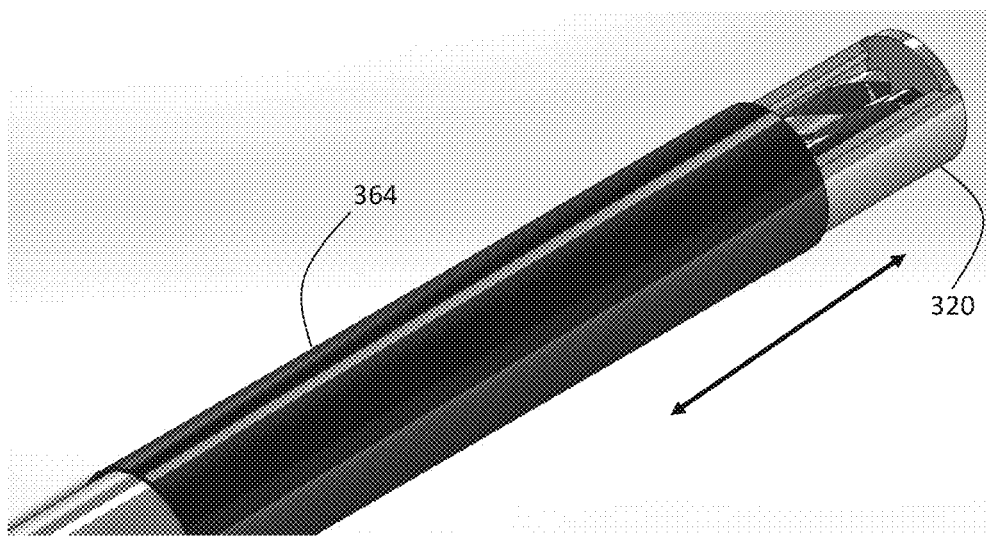
FIG. 32b is a perspective view of the bay sliding sheath assembly of FIG. 32a in a half-open position.
Figure 32C:
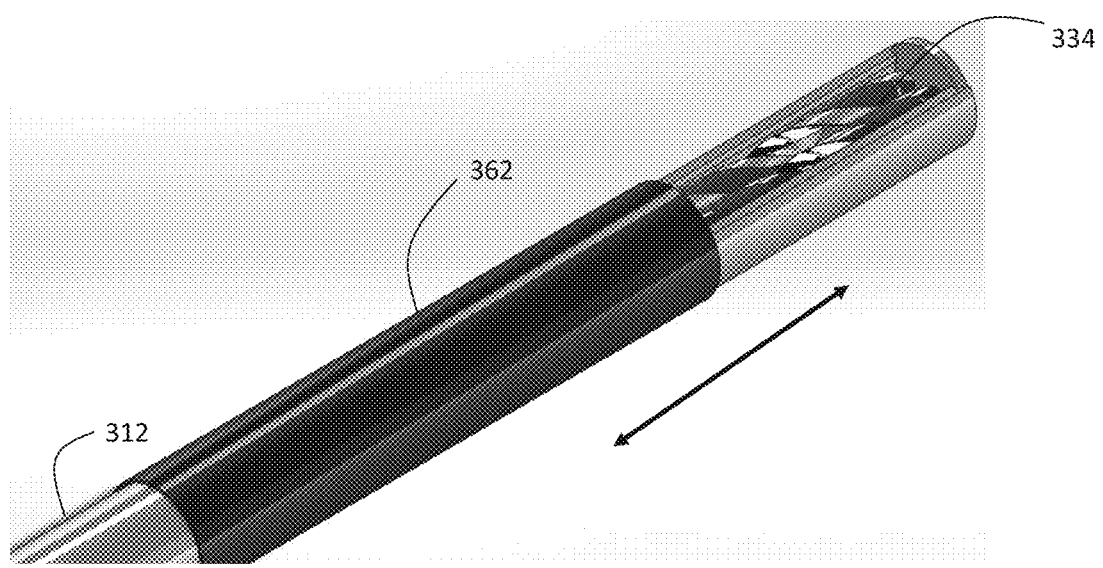
FIG. 32c is a perspective view of the bay sliding sheath assembly of FIG. 32a in an open position.

FIGS. 32a-32c depict a mechanism for covering window 325 using bay sliding outer sheath 364. Bay sliding outer sheath 364 is an outer sheath that typically has no cutouts but slides distally to cover window 325 and slides proximally to expose shredding body. FIG. 32a shows mouth 320 when bay sliding outer sheath 364 has slid distally to fully cover window 325. FIG. 32b depicts mouth 320 when bay sliding outer sheath 364 has slid proximally to expose half of window 325. FIG. 32c depicts mouth 320 when bay sliding outer sheath 364 has slid proximally to the proximal edge of window 325 to fully expose window 325. Bay sliding outer sheath 364 may have any suitable length that facilitates proximal-distal movement. This movement/sliding may be achieved manually if the length extends to proximal body 316 (i.e., outside of the body), or it may be done automatically upon activating a trigger mechanism (not shown) in a conventional manner.

Methodologically, morcellator 300 would be inserted into the subject's body with bay sliding outer sheath 364 slid distally to the distal edge of window 325, thus closing off window 325, as in FIG. 32a. Subsequently, prior to contacting the targeted tissue mass, bay sliding outer sheath 364 can be slid proximally to expose as much of shredding body as desired by the user. For example, if the user desires to morcellate only a relatively small piece of tissue, the user may desire to open only half of window 325, as in FIG. 32b. Alternatively, the user may desire to expose all of shredding body by sliding bay sliding outer sheath 364 fully proximally beyond the proximal edge of window 325.

Definition of Claim Terms

Control apparatus: This term is used herein to refer to any mechanism of controlling the rotation of the jaws and auger. Control can be activation, deactivation, increasing or decreasing speed of rotation, etc.

Cover apparatus: This term is used herein to refer to any mechanism of protecting extraneous tissue from the shredding blades/teeth, typically by covering or filling the window of the mouth. Typically the cover apparatus can be removed or manipulated to expose the shredding blades/teeth within the mouth.

Deploy apparatus: This term is used herein to refer to any mechanism of deploying the cup assembly into an expanded or open position. The deploy apparatus would be dependent on the user's positioning of the cup assembly in compressed position. If the cup assembly is compressed by partially enclosing it in the supplementary channel, then the deploy mechanism of FIG. 16 can be used. However, the deploy apparatus can be manual (as in FIG. 16 for example), automatic, or electronic.

Distal: This term is used herein to refer to proximity to the patient or subject. Thus, the distal end of a structure is closer to the patient or subject than to the user of the morcellator.

Extraneous tissue: This term is used herein to refer to any tissue within the body of the subject or patient that is not being targeted by the user for morcellation.

Gear assembly: This term is used herein to refer to any configuration of gears that facilitates the rotation of the jaws and auger.

Gripping apparatus: This term is used herein to refer to any mechanism of stabilizing or spatially controlling the morcellator. This mechanism can be manual, for example using a handle, or automated/electronic, for example by attachment to machinery (e.g., extension from a robot).

Hook-like protrusion: This term is used herein to refer to a structural part of the blades/teeth that are capable of pinching or grasping tissue during rotation of the jaws.

Inwardly: This term is used herein to refer to the spatial relationship between the jaws and auger relative to the line of path taken by tissue undergoing morcellation. The tissue is cut by the blades/teeth and proceeds further toward the interior of the mouth where the auger is positioned. Thus, the tissue has an inward line of path prior to the auger transporting the tissue proximally toward the gripping mechanism.

Morcellator: This term is used herein to refer to any device used for the removal of tissue from a patient or subject during laparoscopic surgery.

Motor unit: This term is used herein to refer to any mechanism of mechanically powering and controlling the rotation of the jaws and auger.

Opposing blades: This term is used herein to refer to blades/teeth that face each other from their respective jaws if two jaws are present, as may be seen in FIGS. 6, 15, 22, 25*b*, and/or 25*c*. Blades are designed to cut or shred tissue and may have any structure to achieve such function.

Outer edges: This term is used herein to refer to the border of the window of the mouth, or a surface of the mouth that is in proximity to the border of the window.

Pistol grip: This term is used herein to refer to the portion of the morcellator that is held by the user's hand and orients the user's hand in a forward, vertical orientation, or perpendicular to the sheath of the morcellator.

Proximal: This term is used herein to refer to proximity to the user (e.g., surgeon, surgical team) of the morcellator. Thus, the proximal end of a structure is closer to the user of the morcellator than to the patient or subject.

Snugly fits: This term is used herein to refer to the disposition of an elongate structure in a channel, such that the elongate structure is spatially stabilized (i.e., minimal movement around the channel) but is still capable of rotation without damaging the walls of the channel.

Staggered, interlocking relation: This term is used herein to refer to the teeth of each jaw windowing each other, for example as seen in FIG. 15. This configuration of teeth may facilitate the shredding of tissue.

Targeted tissue mass: This term is used herein to refer to the tissue intended to be excised and/or removed from the patient or subject.

Underneath: This term is used herein to refer to a spatial relationship of the auger to the jaws when the morcellator is in an "upright" position or when the sheath is horizontally oriented, as in FIG. 23*d* for example.

Wire frame: This term is used herein to refer to the top edge of the cup assembly, where the wire frame facilitates the expansion of the cup assembly and stabilizes the cup assembly in an upright position. The wire frame can be formed of any suitable material, such as a polymer or metal. Selection of material for the wire frame may be dependent on the needs of the user. For example, a light metal may be desired by the user in order for the wire frame to be able to fold into the supplementary channel in its compressed position but still stabilize the cup assembly in the expanded position.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A morcellator for removing a targeted tissue mass internal to a body of a subject through a laparoscopic port or vagina of said subject, said morcellator comprising:

an elongate sheath having a lumen therewithin along a length of said elongate sheath, said elongate sheath having a proximal end and a distal end;

a mouth forming or coupled to said distal end of said elongate sheath, said mouth having a substantially hollow interior;

a window in said mouth to provide communication between said interior of said mouth and an external environment;

one or more elongate jaws disposed within said lumen of said elongate sheath, said one or more elongate jaws being in fixed spaced relation to each other, said one or more elongate jaws each having a distal end that extends into and terminates in said substantially hollow interior of said mouth, said one or more elongate jaws having blades that draw said targeted tissue mass inwardly into the mouth and lumen of the sheath;

an auger disposed within said lumen of said elongate sheath along said length of said elongate sheath, said auger being in fixed spaced relation underneath said one or more elongate jaws within said substantially hollow interior of said mouth, said auger having a distal end that extends into and terminates in said substantially hollow interior of said mouth, said auger transporting said targeted tissue mass proximally, said lumen of said sheath including a jaw channel that snugly fits each elongate jaw and an auger channel that snugly fits said auger; and a control apparatus for controlling rotation of said each elongate jaw and said auger.

2. A morcellator as in claim 1, further comprising:

a cup assembly positioned in overlying relation to said window of said mouth, said window having outer edges, said cup assembly having a top edge and a bottom edge, said bottom edge of said cup assembly attached to said outer edges of said window, said top edge of said cup assembly formed of a wire frame to stabilizing said cup assembly in an upright position.

3. A morcellator as in claim 2, further comprising:
a supplementary channel disposed along said lumen of said sheath,
said cup assembly having a compressed position and an expanded position, said compressed position being said cup assembly pulled into and partially enclosed by said supplementary channel at a distal end of said supplementary channel.

4. A morcellator as in claim 3, further comprising:
a deploy apparatus that fits within said supplementary channel and deploys said cup assembly from said compressed position to said expanded position.

5. A morcellator as in claim 1, further comprising:
a safety tip positioned at a distal end of said morcellator, said safety tip capable of manipulating extraneous tissue to target said targeted tissue mass.

6. A morcellator as in claim 1, further comprising:
a cover apparatus for covering or filling said window of said mouth, said cover apparatus having a closed position that protects extraneous tissue from said blades and an open position that exposes said blades to said targeted tissue mass.

7. A morcellator as in claim 6, further comprising:
said cover apparatus being a bay rotating outer sheath disposed in outer relation to said mouth, said bay rotating outer sheath including a cutout having a size at least as large as said window.

8. A morcellator as in claim 6, further comprising:
said cover apparatus being a bay sliding outer sheath disposed in outer relation to said elongate sheath and said mouth, said bay sliding outer sheath being slidable in a proximal-distal direction to cover and uncover said mouth.

9. A morcellator as in claim 1, further comprising:
said control apparatus including a motor unit and a gear assembly in communication with said each elongate jaw and said auger.

10. A morcellator as in claim 9, further comprising:
said gear assembly including a plurality of spur gears having a configuration comprising:
  a driving gear securely coupled to said auger,
  a first driven gear meshably engaged to said driving gear,
  a conjointly-rotating driving gear positioned in fixed spaced relation to said first driven gear, said conjointly-rotating driving gear being concentric with said first driven gear, said conjointly-rotating driving gear securely coupled to a first jaw of said one or more elongate jaws, and
  a second driven gear meshably engaged to said conjointly-rotating driving gear, said second driven gear securely coupled to a second jaw of said one or more elongate jaws.

11. A morcellator as in claim 1, further comprising:
said blades including a first set of teeth associated with a first jaw of said one or more jaws and a second set of teeth associated with a second jaw of said one or more jaws, said first and second sets of teeth having a staggered, interlocking relation with each other.

12. A morcellator as in claim 1, further comprising:
hook-like protrusions disposed on said blades to facilitate drawing said targeted tissue mass inwardly between said one or more elongate jaws toward said auger.

13. A morcellator for removing a targeted tissue mass internal to a body of a subject through a laparoscopic port or vagina of said subject, said morcellator comprising:
an elongate sheath having a lumen therewithin along a length of said elongate sheath, said elongate sheath having a proximal end and a distal end;
a mouth forming or coupled to said distal end of said elongate sheath, said mouth having a substantially hollow interior;
a window in said mouth to provide communication between said interior of said mouth and an external environment;
one or more elongate jaws disposed within said lumen of said elongate sheath, said one or more elongate jaws being in fixed spaced relation to each other, said one or more elongate jaws each having a distal end that extends into and terminates in said substantially hollow interior of said mouth, said one or more elongate jaws having blades that draw said targeted tissue mass inwardly into the mouth and lumen of the sheath;
an auger disposed within said lumen of said elongate sheath along said length of said elongate sheath, said auger being in fixed spaced relation underneath said one or more elongate jaws within said substantially hollow interior of said mouth, said auger having a distal end that extends into and terminates in said substantially hollow interior of said mouth, said auger transporting said targeted tissue mass proximally;
a cup assembly positioned in overlying relation to said window of said mouth and lining outer edges of said window; and
a control apparatus for controlling rotation of said each elongate jaw and said auger.

14. A morcellator as in claim 13, further comprising:
said lumen of said sheath including a jaw channel that snugly fits said each elongate jaw and an auger channel that snugly fits said auger.

15. A morcellator as in claim 13, further comprising:
said cup assembly having a top edge and a bottom edge, said bottom edge of said cup assembly attached to said outer edges of said window, said top edge of said cup assembly formed of a wire frame to stabilizing said cup assembly in an upright position.

16. A morcellator as in claim 15, further comprising:
a supplementary channel disposed along said lumen of said sheath,
said cup assembly having a compressed position and an expanded position, said compressed position being said cup assembly pulled into and partially enclosed by said supplementary channel at a distal end of said supplementary channel.

17. A morcellator as in claim 16, further comprising:
a deploy apparatus that fits within said supplementary channel and deploys said cup assembly from said compressed position to said expanded position.

18. A morcellator as in claim 13, further comprising:
a safety tip positioned at a distal end of said morcellator, said safety tip capable of manipulating extraneous tissue to target said targeted tissue mass.

19. A morcellator as in claim 13, further comprising:
a cover apparatus for covering or filling said window of said mouth, said cover apparatus having a closed position that protects extraneous tissue from said blades and an open position that exposes said blades to said targeted tissue mass.

20. A morcellator as in claim 19, further comprising:
said cover apparatus being a bay rotating outer sheath disposed in outer relation to said mouth, said bay rotating outer sheath including a cutout having a size at least as large as said window.

21. A morcellator as in claim 19, further comprising:
said cover apparatus being a bay sliding outer sheath disposed in outer relation to said elongate sheath and said mouth, said bay sliding outer sheath being slidable in a proximal-distal direction to cover and uncover said mouth.

22. A morcellator as in claim 13, further comprising:
said control apparatus including a motor unit and a gear assembly in communication with said each elongate jaw and said auger.

23. A morcellator as in claim 22, further comprising:
said gear assembly including a plurality of spur gears having a configuration comprising:
- a driving gear securely coupled to said auger,
- a first driven gear meshably engaged to said driving gear,
- a conjointly-rotating driving gear positioned in fixed spaced relation to said first driven gear, said conjointly-rotating driving gear being concentric with said first driven gear, said conjointly-rotating driving gear securely coupled to a first jaw of said one or more elongate jaws, and
- a second driven gear meshably engaged to said conjointly-rotating driving gear, said second driven gear securely coupled to a second jaw of said one or more elongate jaws.

24. A morcellator as in claim 13, further comprising:
said blades including a first set of teeth associated with a first jaw of said one or more jaws and a second set of teeth associated with a second jaw of said one or more jaws, said first and second sets of teeth having a staggered, interlocking relation with each other.

25. A morcellator as in claim 13, further comprising:
hook-like protrusions disposed on said blades to facilitate drawing said targeted tissue mass inwardly between said one or more elongate jaws toward said auger.

* * * * *